(12) United States Patent
Yamada

(10) Patent No.: US 10,895,692 B2
(45) Date of Patent: Jan. 19, 2021

(54) FIBER OPTIC ROTARY JOINTS AND METHODS OF USING AND MANUFACTURING SAME

(71) Applicant: Canon USA, Inc., Melville, NY (US)

(72) Inventor: Daisuke Yamada, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 151 days.

(21) Appl. No.: 15/965,035

(22) Filed: Apr. 27, 2018

(65) Prior Publication Data
US 2018/0348439 A1   Dec. 6, 2018

Related U.S. Application Data

(60) Provisional application No. 62/513,829, filed on Jun. 1, 2017.

(51) Int. Cl.
*G01B 9/02* (2006.01)
*G02B 6/36* (2006.01)
(Continued)

(52) U.S. Cl.
CPC .......... *G02B 6/3604* (2013.01); *A61B 5/6852* (2013.01); *G01B 9/02091* (2013.01);
(Continued)

(58) Field of Classification Search
CPC .... G02B 6/3604; G02B 6/29362; G02B 6/32; G02B 6/3628; A61B 5/6852;
(Continued)

(56) References Cited

U.S. PATENT DOCUMENTS 5,337,734 A   8/1994   Saab
5,347,990 A   9/1994   Ebling et al.
(Continued)

FOREIGN PATENT DOCUMENTS

CN   103995321 A   8/2014
JP   05160492 A1   6/1993
(Continued)

OTHER PUBLICATIONS

The partial European search report (R. 64 EPC) for European Application No. 18174723.9-1124, dated Nov. 12, 2018.
(Continued)

*Primary Examiner* — Tarifur R Chowdhury
*Assistant Examiner* — Jonathon Cook
(74) *Attorney, Agent, or Firm* — Canon U.S.A., Inc. I.P. Division

(57) ABSTRACT

One or more fiber optic rotary joints (FORJ), free space beam combiners, OCT, SEE and/or fluorescence devices and systems for use therewith, methods of manufacturing same and storage mediums are provided. One or more embodiments of FORJs may be used with numerous applications in the optical field, including, but not limited to, OCT and fluorescence applications. Examples of such applications include imaging, evaluating and diagnosing biological objects, such as, but not limited to, for Gastro-intestinal, cardio and/or ophthalmic applications, and being obtained via one or more optical instruments.

22 Claims, 13 Drawing Sheets

(51) Int. Cl.
  *A61B 5/00* (2006.01)
  *G02B 6/293* (2006.01)
  *G02B 6/32* (2006.01)
(52) U.S. Cl.
  CPC ........ *G02B 6/29362* (2013.01); *A61B 5/0035* (2013.01); *A61B 5/0066* (2013.01); *A61B 5/0071* (2013.01); *G02B 6/32* (2013.01)
(58) Field of Classification Search
  CPC ... A61B 5/0035; A61B 5/0066; A61B 5/0071; G01B 9/02091; G01B 9/02029
  See application file for complete search history.

(56) References Cited

U.S. PATENT DOCUMENTS

| | | | |
|---|---|---|---|
| 5,371,814 | A | 12/1994 | Ames et al. |
| 5,588,077 | A | 12/1996 | Woodside |
| 6,341,036 | B1 | 1/2002 | Tearney et al. |
| 6,773,170 | B1 | 8/2004 | Georgiev et al. |
| 7,366,376 | B2 | 4/2008 | Shishkov et al. |
| 7,447,408 | B2 | 11/2008 | Bouma et al. |
| 7,551,293 | B2 | 6/2009 | Yelin et al. |
| 7,724,996 | B2 | 5/2010 | Popp et al. |
| 7,796,270 | B2 | 9/2010 | Yelin et al. |
| 7,843,572 | B2 | 11/2010 | Tearney et al. |
| 7,859,679 | B2 | 12/2010 | Bouma et al. |
| 7,872,759 | B2 | 1/2011 | Tearney et al. |
| 7,889,348 | B2 | 2/2011 | Tearney et al. |
| 8,045,177 | B2 | 10/2011 | Tearney et al. |
| 8,145,018 | B2 | 3/2012 | Shishkov et al. |
| 8,289,522 | B2 | 10/2012 | Tearney et al. |
| 8,380,024 | B1 | 2/2013 | Zhang et al. |
| 8,384,909 | B2 | 2/2013 | Yun et al. |
| 8,679,002 | B2 | 3/2014 | Sutoh et al. |
| 8,830,024 | B2 | 9/2014 | Buettner |
| 8,838,213 | B2 | 9/2014 | Tearney et al. |
| 8,928,889 | B2 | 1/2015 | Tearney et al. |
| 8,953,911 | B1 | 2/2015 | Xu et al. |
| 9,086,533 | B1 | 7/2015 | Wach |
| 9,087,368 | B2 | 7/2015 | Tearney et al. |
| 9,254,089 | B2 | 2/2016 | Tearney et al. |
| 9,295,391 | B1 | 3/2016 | Tearney et al. |
| 9,332,942 | B2 | 5/2016 | Jaffer et al. |
| 9,415,550 | B2 | 8/2016 | Tearney et al. |
| 9,557,154 | B2 | 1/2017 | Tearney et al. |
| 9,968,261 | B2 | 5/2018 | Motafakker-Fard et al. |
| 2002/0146227 | A1 | 10/2002 | Suzuki et al. |
| 2007/0217736 | A1 | 9/2007 | Zhang et al. |
| 2008/0175535 | A1 | 7/2008 | Popp et al. |
| 2008/0175536 | A1 | 7/2008 | Krumme |
| 2008/0267562 | A1 | 10/2008 | Wang et al. |
| 2009/0027689 | A1 | 1/2009 | Yun et al. |
| 2009/0244545 | A1* | 10/2009 | Toida ................... A61B 5/0066 356/477 |
| 2009/0310911 | A1 | 12/2009 | Zhang et al. |
| 2010/0092389 | A1 | 4/2010 | Jaffer |
| 2010/0228119 | A1* | 9/2010 | Brennan .................. A61B 3/10 600/424 |
| 2011/0292400 | A1 | 12/2011 | Fleming et al. |
| 2012/0022360 | A1* | 1/2012 | Kemp .................. A61B 5/6852 600/410 |
| 2012/0101374 | A1 | 4/2012 | Tearney et al. |
| 2013/0163939 | A1 | 6/2013 | Doric |
| 2013/0206967 | A1 | 8/2013 | Shpunt et al. |
| 2015/0285683 | A1* | 10/2015 | Ouellette .............. G01J 3/0218 356/451 |
| 2016/0045102 | A1 | 2/2016 | Yu |
| 2016/0228097 | A1 | 8/2016 | Jaffer et al. |
| 2016/0341951 | A1 | 11/2016 | Tearney et al. |
| 2017/0035281 | A1 | 2/2017 | Takeuchi et al. |
| 2017/0135584 | A1 | 5/2017 | Tearney et al. |
| 2017/0167861 | A1 | 6/2017 | Chen et al. |
| 2017/0168232 | A1 | 6/2017 | Tearney et al. |
| 2017/0176736 | A1 | 6/2017 | Yamamoto et al. |
| 2017/0209049 | A1 | 7/2017 | Wang et al. |
| 2017/0322079 | A1 | 11/2017 | Do et al. |
| 2018/0017778 | A1 | 1/2018 | Ikuta et al. |

FOREIGN PATENT DOCUMENTS

| | | |
|---|---|---|
| JP | 2009-236614 A | 10/2009 |
| WO | 2001/016635 A1 | 3/2001 |
| WO | 2009/137659 A1 | 11/2009 |
| WO | 2015/116939 A1 | 8/2015 |
| WO | 2015/116951 A2 | 8/2015 |
| WO | 2015/117241 A1 | 8/2015 |
| WO | 2017/024145 A1 | 2/2017 |
| WO | 2017/117203 A1 | 7/2017 |
| WO | 2017/139657 A1 | 8/2017 |
| WO | 2017165511 A1 | 9/2017 |
| WO | 2018140875 A1 | 8/2018 |

OTHER PUBLICATIONS

Kang, D., et al., "Minature grating for spectrally-encoded endoscopy", Lab Chip, 2013, Published Feb. 25, 2013, pp. 1810-1816, vol. 13.

Kang, D., et al., "Spectrally-encoded color imaging", Optics Express, Aug. 17, 2009, pp. 15239-15247, vol. 17, No. 17.

Yelin, D., et al., "Three-dimensional miniature endoscopy", Nature, Oct. 19, 2006, pp. 765, vol. 443.

Zeidan, A., et al. "Miniature forward-viewing spectrally encoded endoscopic probe", Optics Letters, Aug. 15, 2014, pp. 4871-4874, vol. 39, Issue 16.

* cited by examiner

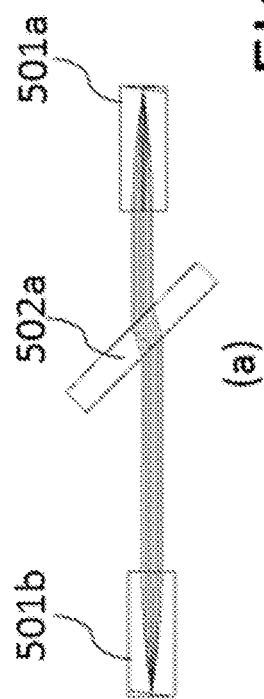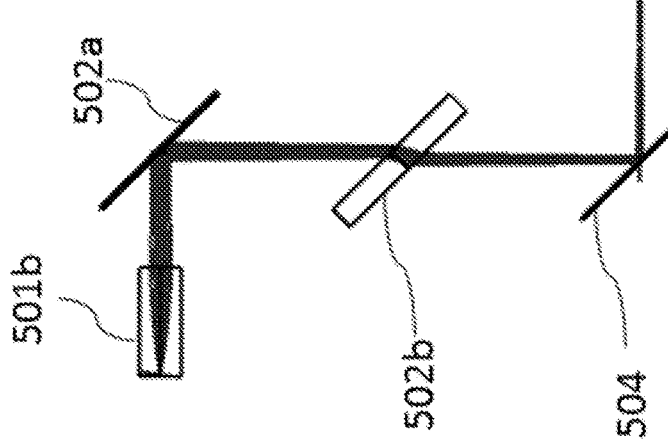
FIG. 6a
FIG. 6b

FIBER OPTIC ROTARY JOINTS AND METHODS OF USING AND MANUFACTURING SAME

CROSS-REFERENCE TO RELATED APPLICATION(S)

This application relates, and claims priority, to U.S. Patent Application Ser. No. 62/513,829, filed Jun. 1, 2017, the entire disclosure of which is incorporated by reference herein in its entirety.

FIELD OF THE INVENTION

The present disclosure relates generally to the field of optical imaging and more particularly to fiber optic rotary joints that may be used with one or more optical apparatuses, systems, methods (for using and/or manufacturing) and storage mediums, such as, but not limited to, fiber optic catheters, endoscopes and/or optical coherence tomography (OCT) and/or fluorescence apparatuses and systems, and methods and storage mediums, for use with same, to achieve structural compactness and high coupling efficiency. Examples of optical applications that may involve the use of a fiber optic rotary joint include imaging, evaluating and characterizing/identifying biological objects or tissue, such as, but not limited to, for gastro-intestinal, otolaryngologic, cardio and/or ophthalmic applications.

BACKGROUND OF THE INVENTION

Fiber optic catheters and endoscopes have been developed to access to internal organs. For example in cardiology, OCT (optical coherence tomography) has been developed to see depth resolved images of vessels with a catheter. The catheter, which may include a sheath, a coil and an optical probe, may be navigated to a coronary artery.

Optical coherence tomography (OCT) is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are. Single mode fibers are commonly used for OCT optical probes, and double clad fibers are also commonly used for fluorescence and/or spectroscopy.

Spectrally encoded endoscope (SEE) is an endoscope technology which uses a broadband light source, a rotating or oscillating grating and a spectroscopic detector to encode spatial information from a sample. When illuminating light to the sample, the light is spectrally dispersed along one illumination line, such that the dispersed light illuminates a specific position of the illumination line with a specific wavelength. When the reflected light from the sample is detected with a spectrometer, the intensity distribution is analyzed as the reflectance along the line where the wavelength encodes the spatial information. By rotating or oscillating the grating to scan the illumination line, a two-dimensional image of the sample is obtained.

In order to acquire cross-sectional images of tubes and cavities such as vessels, and/or esophagus and nasal cavities, the optical probe is rotated with a fiber optic rotary joint (FORJ). A FORJ is the interface unit that operates to rotate one end of a fiber and/or an optical probe. In general, a free space beam coupler is assembled to separate a stationary fiber and a rotor fiber inside the FORJ. Besides, the optical probe may be simultaneously translated longitudinally during the rotation so that helical scanning pattern images are obtained. This translation is most commonly performed by pulling the tip of the probe back along a guidewire towards a proximal end and, therefore, referred to as a pullback.

A multi-modality system such as an OCT, fluorescence, and/or spectroscopy system with an optical probe is developed to obtain multiple information at the same time. The multi-modality FORJ has a beam combiner for at least two beams with multiple wavelengths to couple into the probe. Generally, lenses are assembled to make collimated beams for both stationary and rotor fibers in the beam combiner. Further, the detected light may be collected in the same or in one or more additional fibers, and, if rotating, these additional fibers may structurally interfere with each other.

It is difficult to make collimated beams for the common rotor fibers with different wavelengths, especially when the wavelength differences are large (e.g., in the range of 630 nm to 1300 nm, about double, etc.). An achromatic lens could be used to correct chromatic aberration; however, it is still difficult to control beam waist positions with multiple wavelengths to have high coupling efficiencies. Also, lenses with corrected aberrations are undesirably large, so a FORJ would become undesirably large (e.g., focal length and lens material(s) may increase size as well).

Accordingly, it would be desirable to provide at least one FORJ for use in at least one optical device, assembly or system to address one or more of the aforementioned inefficient and wasteful drawbacks, especially in a way that reduces or minimizes cost of manufacture, maintenance and/or use and/or in a way that achieves a compact FORJ with high coupling efficiency.

SUMMARY OF THE INVENTION

Accordingly, it is a broad object of the present disclosure to provide fiber optic rotary joints that may be used with one or more optical apparatuses, systems, methods (for using and/or manufacturing) and storage mediums, such as, but not limited to, fiber optic catheters, endoscopes and/or optical coherence tomography (OCT) apparatuses and systems, and methods and storage mediums, for use with same, to achieve structural compactness and high coupling efficiency. One or more additional objects of the present disclosure are to provide an easy way to fabricate a free space optical beam combiner and to provide an easy way to manufacture one or more FORJs. At least one further object of the present disclosure is to provide a new optical path configuration(s) to control beams with multiple wavelengths independently so that a compact FORJ with high coupling efficiency may be achieved.

In accordance with one or more embodiments of the present disclosure, apparatuses and systems, and methods and storage mediums for use with one or more embodiments of a FORJ may operate to characterize biological objects, such as, but not limited to, blood, mucus, tissue, etc.

In accordance with one or more aspects of the present disclosure, at least one embodiment of a FORJ in an apparatus or system may relate to forward and side views or imaging. Additionally or alternatively, one or more embodiments of a FORJ in an apparatus or system may relate to using a photo diode. At least one embodiment may obtain one or more types of images (e.g., SEE, OCT, etc.).

One or more embodiments of the present disclosure may be used in clinical application(s), such as, but not limited to, intervascular imaging, atherosclerotic plaque assessment, cardiac stent evaluation, balloon sinuplasty, sinus stenting, arthroscopy, ophthalmology, ear research, veterinary use and research, etc.

In accordance with at least another aspect of the present disclosure, the FORJs and one or more technique(s) discussed herein may be employed to reduce the cost of at least one of manufacture and maintenance of the FORJ(s) in one or more devices, systems and storage mediums by reducing or minimizing a number of optical components in an interference optical system, such as an interferometer and/or such as using other light sources including LEDs (e.g., when sensitivity is sufficient and/or meets a predetermined condition, threshold or requirement) to cut down cost.

According to other aspects of the present disclosure, one or more additional devices, one or more systems, one or more methods and one or more storage mediums using, or for use with, one or more FORJs are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIGS. 6a-6c are a diagram showing an optical ray-trace simulation obtained using zemax for one or more components of at least one embodiment of a fiber optic rotary joint in accordance with one or more aspects of the present disclosure;

DETAILED DESCRIPTION OF THE PRESENT INVENTION

One or more devices, optical systems, methods and storage mediums for imaging using a fiber optic rotary joint, and one or more methods of manufacturing at least one fiber optic rotary joint and/or of manufacturing at least one free space optical beam combiner, are disclosed herein.

Figure 1:
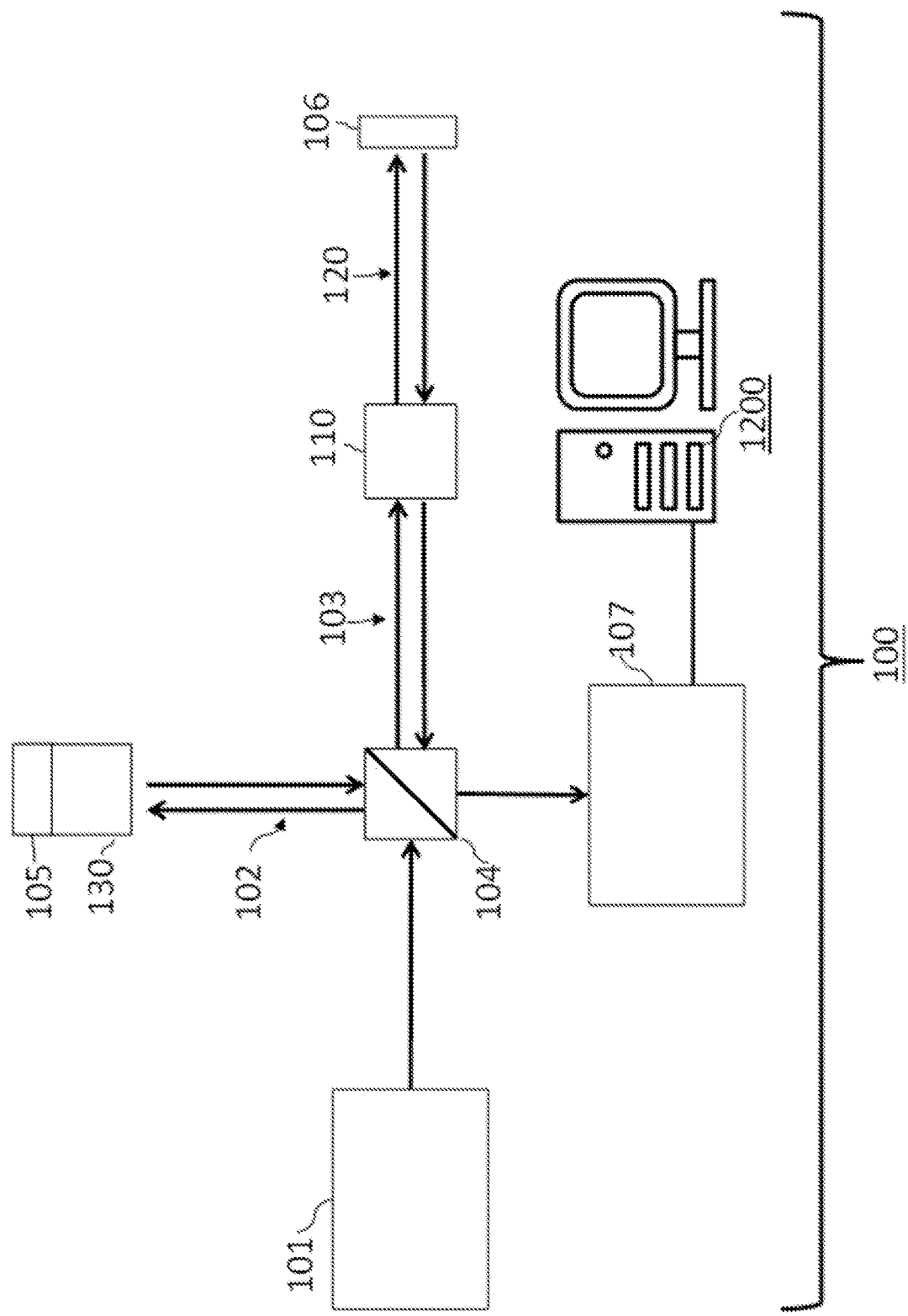
FIG. 1 is a diagram showing an embodiment of a system which can utilize a fiber optic rotary joint in accordance with one or more aspects of the present disclosure.

Turning now to the details of the figures, FIG. 1 shows an OCT system 100 (as referred to herein as "system 100" or "the system 100") which operates to utilize an OCT technique with optical probe applications in accordance with one or more aspects of the present disclosure. The system 100 comprises a light source lot, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 130. In one or more embodiments, the system 100 may include a patient interface device or unit ("PIU") 110 and a catheter 120 (as diagrammatically shown in FIGS. 1-3), and the system 100 may interact with a sample 106 (e.g., via the catheter 120 and/or the PIU 110). In one or more embodiments, the system 100 includes an interferometer or an interferometer is defined by one or more components of the system 100, such as, but not limited to, at least the light source lot, the reference arm 102, the sample arm 103, the splitter 104 and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample 106. The reference beam goes through the phase shift unit 130 (when included in a system, as shown in the system 100), and the reference beam is reflected from the reference mirror 105 in the reference arm 102 while the sample beam is reflected or scattered from a sample 106 through the PIU (patient interface unit) 110 and the catheter 120 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200, 1200' (shown in FIG. 11 or FIG. 12, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which can then be split up into at least three bands in which each band is further dispersed to provide light which then used to for spectral encoding of spatial information. The light source lot may be fiber coupled or may be free space coupled to the other components of the system or systems discussed herein, such as, but not limited to, the system 100, the system 100', etc.

In accordance with at least one aspect of the present disclosure, a feature of OCT systems is implemented using fiber optics. As aforementioned, one application of an OCT technique of the present disclosure is to use OCT with a catheter 120 as schematically shown in FIGS. 1-3.

Figure 2:
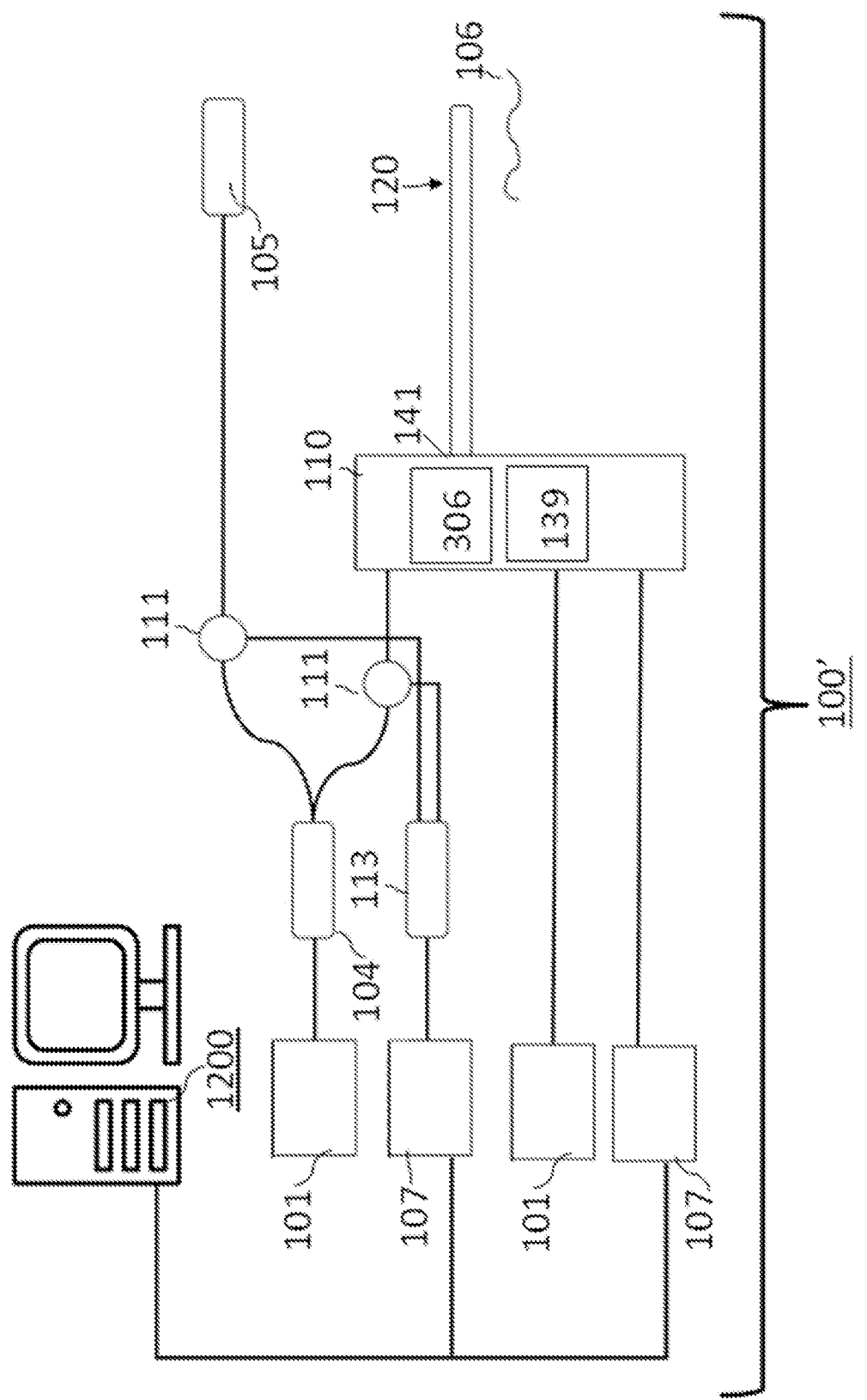
FIG. 2 is a diagram showing an embodiment of a system which can utilize a fiber optic rotary joint in accordance with one or more aspects of the present disclosure.
Figures 11, 12:
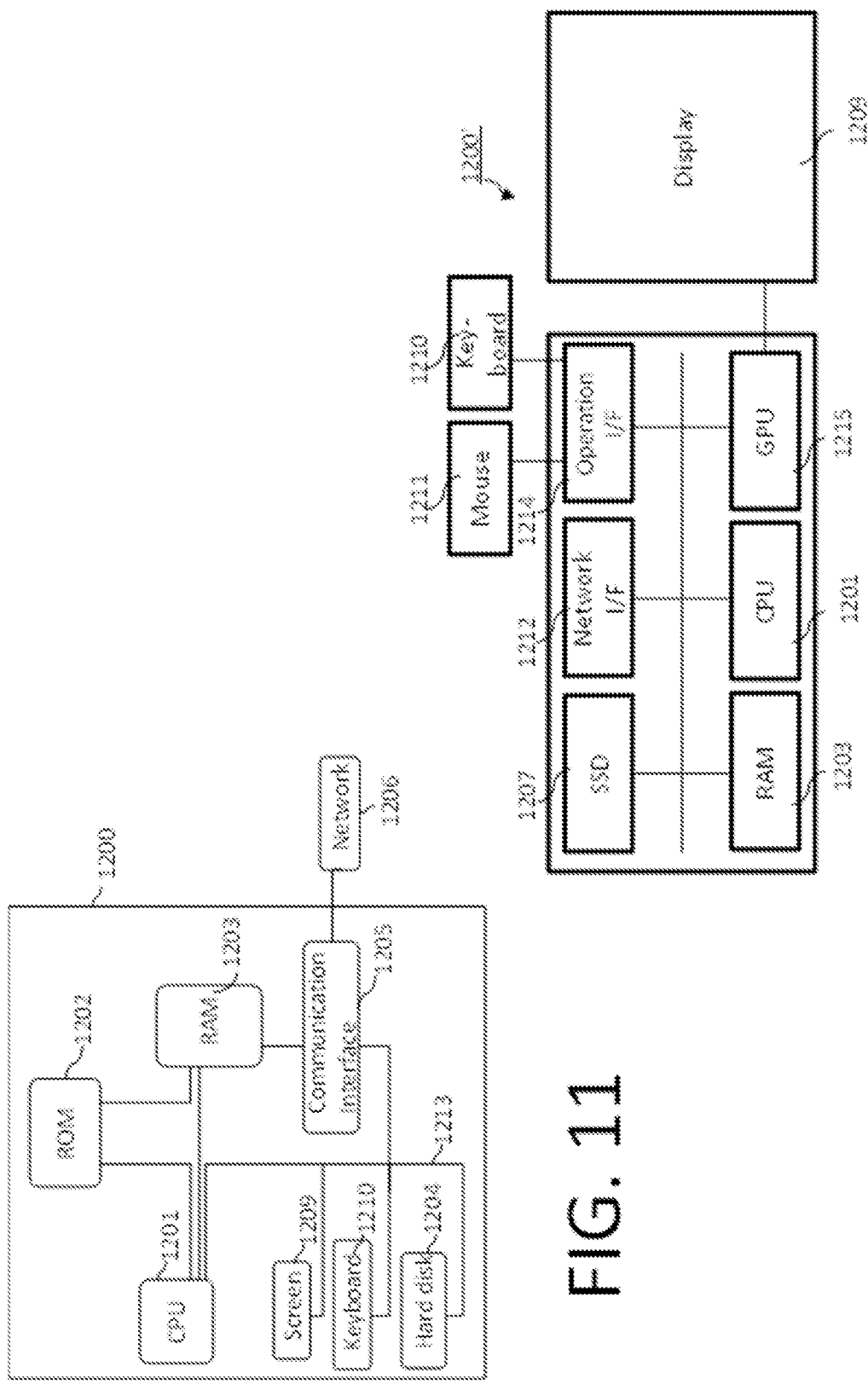
FIG. 11 shows a schematic diagram of an embodiment of a computer that may be used with one or more embodiments of a fiber optic rotary joint in accordance with one or more aspects of the present disclosure.
FIG. 12 shows a schematic diagram of another embodiment of a computer that may be used with one or more embodiments of a fiber optic rotary joint in accordance with one or more aspects of the present disclosure.

FIG. 2 shows at least one embodiment of a system 100' which includes OCT and fluorescence sub-systems. In one or more embodiments, the OCT sub-system includes a light source, such as the light source 101, a splitter (such as the splitter 104; another type of deflecting or deflection device discussed below may be used in place of the splitter 104), one or more circulators 111, a reference reflection (such as the reference reflection 105), a combiner (such as the combiner 113), and at least one detector (such as the at least one detector 107). The OCT sub-system may be connected to, and include, a patient interface unit, such as the PIU 110, and the catheter 120 to expose a sample, such as the sample 106, to light and receive information in response thereto. In one or more embodiments, the fluorescence sub-system may include a light source for fluorescence (such as the second light source lot shown in FIG. 2) and at least one detector (such as the second at least one detector 107 shown in FIG. 2). The fluorescence sub-system, including, but not limited to, the second light source lot and the second at least one detector 107, may also be connected to (see FIG. 2), and/or include, a patient interface unit, such as the PIU 110, and the catheter 120 to expose a sample, such as the sample 106, to fluorescent light and receive information in response thereto. For example, in at least one embodiment, an OCT light with a wavelength of around 1.3 um from a light source (such as the light source 101 of the OCT sub-system) is delivered and split into a reference arm (e.g., the reference arm 102) and a sample arm (e.g., the sample arm 103) with a splitter (e.g., the splitter 104). A reference beam is reflected from a reference mirror (e.g., the reference reflection 105) in the reference arm (e.g., the reference arm 102) while a sample beam is reflected or scattered from a sample through a PIU (patient interface unit) (such as the PIU 110) and a catheter (e.g., the catheter 120) in the sample arm (e.g., the sample arm 103). Both beams combine at a combiner (e.g., the splitter 104 in FIG. 1, the combiner 113 in FIG. 2, etc.) and generate interference patterns. The output of the interferometer is detected with detectors (e.g., the at least one detector 107 shown in FIG. 1, the at least one detector 107 of the OCT sub-system shown in FIG. 2, etc.) such as photodiodes or multi-array cameras. Then signals are transferred to a computer (e.g., the computer 1200 as shown in FIGS. 1-2 and 11, the computer 1200' of FIG. 12, etc.) to perform signal processing. The interference patterns are generated only when the path length of the sample arm (e.g., the sample arm 103) matches that of the reference arm (e.g., the reference arm 102) to within the coherence length of the light source (e.g., the light source 101 of FIG. 1, the light source 101 of the OCT sub-system of FIG. 2, etc.).

An excitation light with a wavelength (e.g., any predetermined wavelength visible to infrared (IR)), for example, 0.633 um from a light source (e.g., the light source 101 of the fluorescence sub-system of FIG. 2) is delivered to the sample (e.g., the sample 106) through the PIU (e.g., the PIU 110) and the catheter (e.g., the catheter 120). The sample (e.g., the sample 106) emits auto-fluorescence light with broadband wavelengths of, for example, 0.633 um-0.80 um by the excitation light. The auto-fluorescence light is collected with the catheter (e.g., the catheter 120 of FIG. 2) and delivered to detectors (e.g., the detector(s) 107 of the fluorescence sub-system of FIG. 2) via the PIU (e.g., the PIU 110). Other wavelengths, in the visible and NIR are also contemplated.

Figure 3:
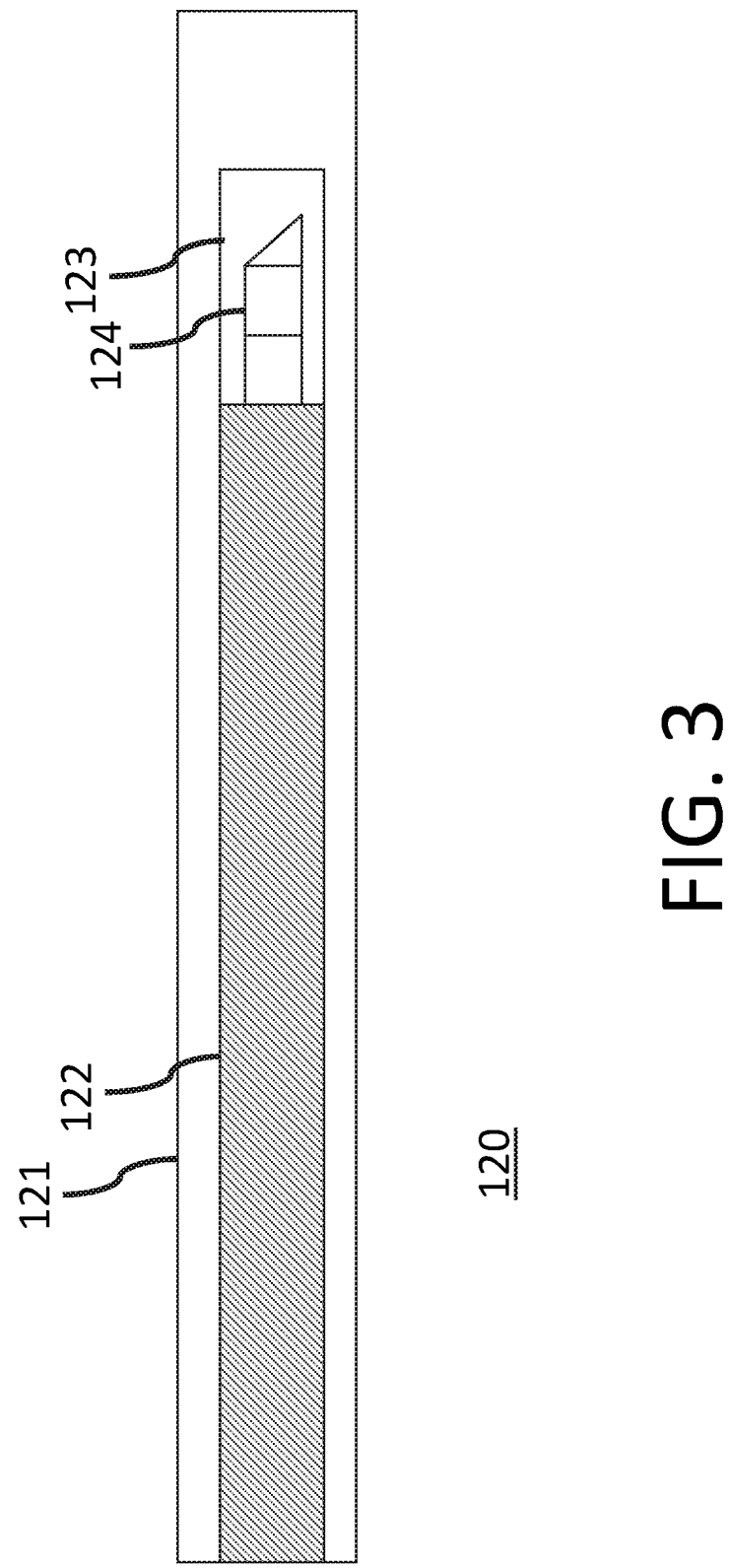
FIG. 3 is a diagram of an embodiment of a catheter that may used with at least one embodiment of a fiber optic rotary joint in accordance with one or more aspects of the present disclosure.

FIG. 3 shows an embodiment of the catheter 120 including a sheath 121, a coil 122, a protector 123 and an optical probe 124. As shown schematically in FIGS. 1-2, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 1) of an OCT interferometer in order to provide access to internal organs, such as intravascular images, gastrointestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation is most commonly performed by pulling the tip of the probe 124 back towards the proximal end and therefore referred to as a pullback.

In at least one embodiment, there is a mirror (e.g., mirror 504 of FIGS. 4-5 as discussed below) at the distal end so that the light beam is deflected outward. In at least one embodiment, the optical probe 124 comprises a fiber connector at a proximal end, a double clad fiber and a lens at a distal end. The fiber connector may be connected with the PIU 110. The double clad fiber (see e.g., double clad fiber 506 of FIGS. 4-5 as discussed below) is used to deliver both OCT and fluorescence lights. The lens (see e.g., GRIN lens 501b shown in FIG. 4 as discussed below) is used for focusing and collecting lights to and/or from the sample (e.g., the sample 106).

In one or more embodiments, the patient user interface 110 may comprise or include a connection component (or interface module), such as a rotary junction (e.g., the rotary junction 306 as shown schematically in FIGS. 2 and 4-7, another rotary junction discussed herein, etc.), to connect one or more components, such as one or more components of a probe (e.g., a catheter 120 (see e.g., FIGS. 1-3)), a needle, a capsule, a patient interface unit (e.g., the patient interface unit 110), etc., to one or more other components, such as, an optical component, a light source (e.g., the light source 101), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc.), the sample arm 102, a motor that operates to power the connection component and/or the patient user interface 110, etc. For example, when the connection member or interface module is a rotary junction, preferably the rotary junction operates in the same or similar fashion as the rotary junction 306 discussed herein). In one or more other embodiments, the rotary junction may be at least one of: a contact rotary junction, a lenseless rotary junction, a lens-based rotary junction, or other rotary junction known to those skilled in the art.

Figure 4:
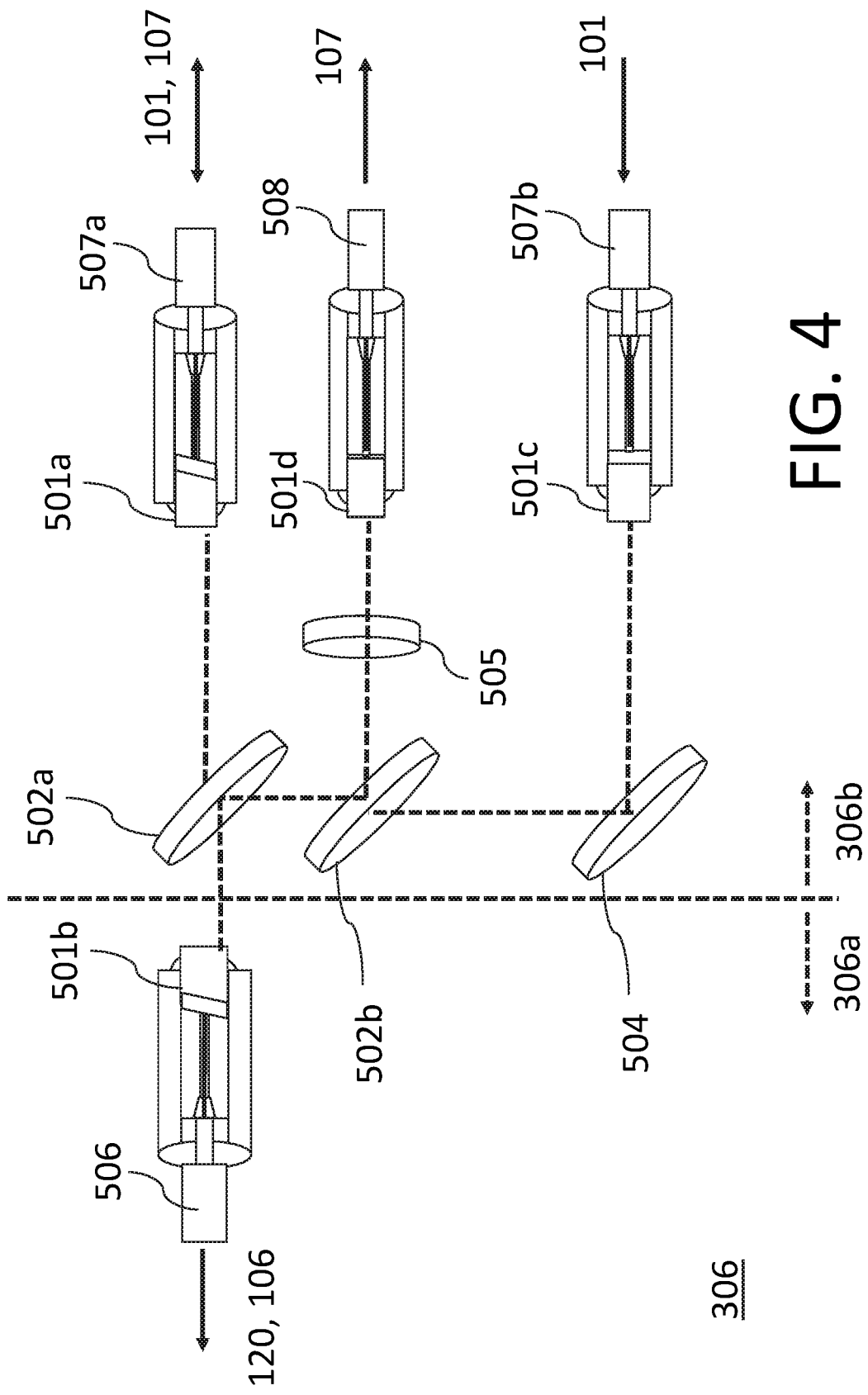
FIG. 4 is a diagram showing an embodiment of a fiber optic rotary joint in accordance with one or more aspects of the present disclosure.
Figure 5:
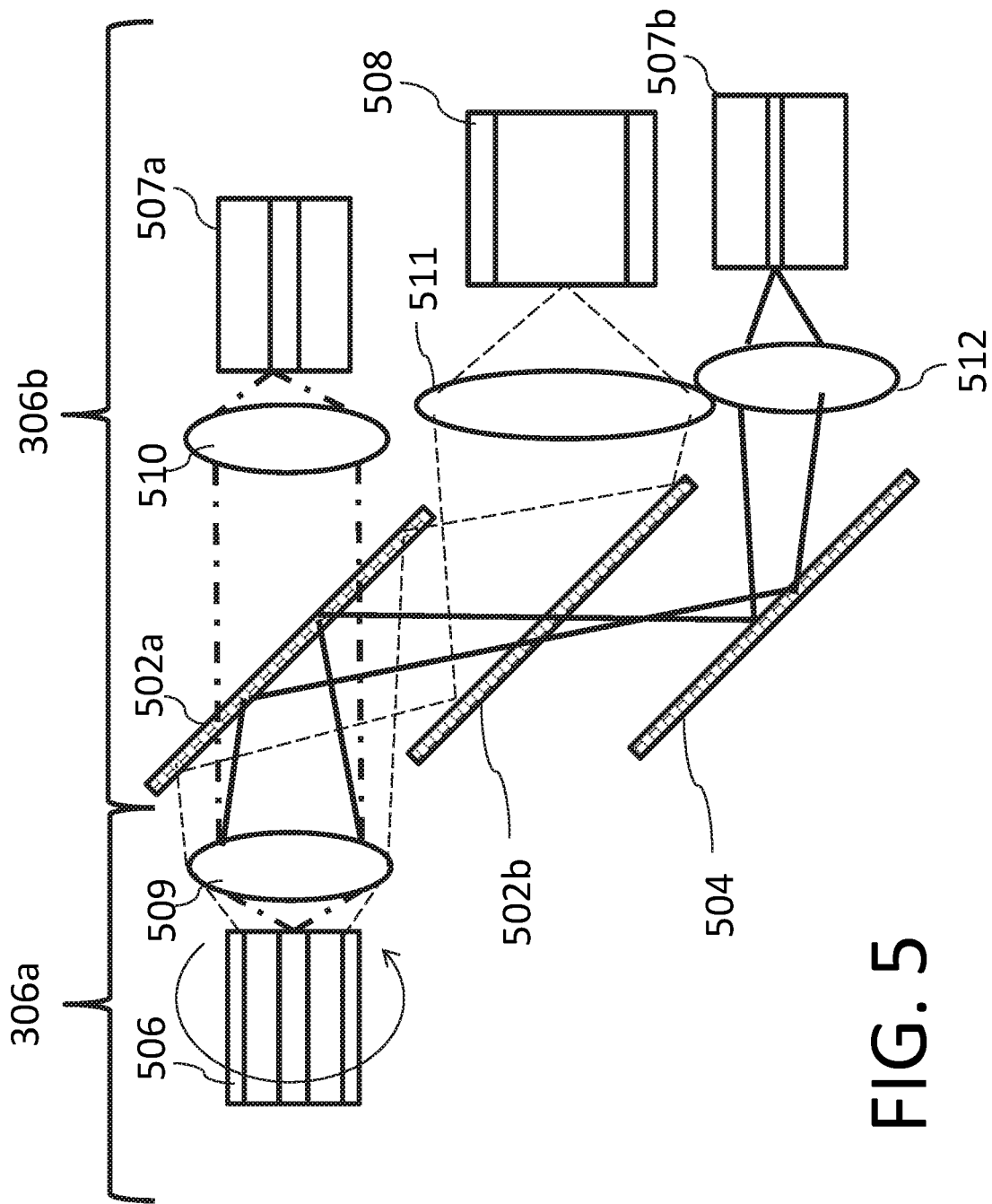
FIG. 5 is a schematic diagram showing an example of light passing through an embodiment of a fiber optic rotary joint in accordance with one or more aspects of the present disclosure.

In at least one embodiment, the PIU 110 may include a FORJ (such as the rotary joint 306 discussed herein), a rotational motor and translation motorized stage (see e.g., portion 139 of PIU 110 as shown in FIG. 2), and a catheter connector (see e.g., portion 141 of the PIU 110 as shown in FIG. 2). The FORJ allows uninterrupted transmission of an optical signal while rotating the double clad fiber (e.g., the DCF 506) along the fiber axis. The FORJ has a free space optical beam combiner consisting of a rotor and stator (see e.g., rotor 306a and stator 306b as shown in FIGS. 4-5 and as discussed further below). FIG. 4 shows a configuration of a free space beam combiner and FORJ in accordance with at least one embodiment of the present disclosure. In an OCT and fluorescence system (such as the system 100' as shown in FIG. 2), the stator (e.g., the stator 306b of FIG. 4) comprises at least two (2) optical fibers for OCT and excitation (see e.g., single mode fiber 507a of FIG. 4 that operates for OCT light source delivery and light detection; single mode fiber 507b of FIG. 4 that operates to work with the excitation light source 107 (e.g., light source 101 of the fluorescence sub-system or portion of system 100' of FIG. 2); etc.). Each fiber has a lens at the beam combiner side of each fiber (e.g., the single mode fiber 507a is connected to a GRIN lens 501a as shown in FIG. 4; the multi-mode fiber 508 is connected to a GRIN lens 501d as shown in FIG. 4; the single mode fiber 507b is connected to a GRIN lens 501c as shown in FIG. 4; etc.). The rotor (e.g., the rotor 306a of FIG. 4) is made of a double clad fiber (e.g., the double clad fiber 506) with a fiber connection at the catheter (e.g., the catheter 120) side and a lens (e.g., a GRIN lens 501b as shown in FIG. 4) at the beam combiner side. Then, the fiber connector of the rotor (e.g., the rotor 306a) is connected to the optical probe (e.g., the optical probe 124 via the catheter 120 as shown in FIGS. 3-4), and the stator (e.g., the stator 306b) is connected to the optical sub-systems (as shown schematically in FIGS. 4-5). For example, in at least one embodiment as best seen schematically in FIG. 4, the single mode fiber 507a is connected to the OCT light source (e.g., the light source 101) and the detection elements (e.g., the at least one detector 107) of the OCT sub-system, the multi-mode fiber 508 is connected to the fluorescence detection elements (e.g., the at least one detector 107) of the fluorescence sub-system), and the single mode fiber 507b is connected to the excitation light source (e.g., the light source 101) of the fluorescence sub-system. The rotational motor (e.g., the rotational motor 139) delivers the torque to the rotor (e.g., the rotor 306a). Also, the translation motorized stage is used for a pullback such that the beam is scanned inside the lumen sample in a helical manner. The catheter connector (e.g., the catheter connector 141 as shown schematically in FIG. 2) is connected to the catheter (e.g., the catheter 120).

As best seen in FIG. 4, OCT light is collimated with a GRIN lens 501a from single mode fiber 507a. The collimated OCT light couples into the core of the double clad fiber 506 (of rotor 306a) via a dichroic filter 502a and a GRIN lens 501b. Also, the back scattered OCT light from the sample (e.g., the sample 106) goes back to the rotor 306a (via the catheter 120). The light is collimated with the GRIN lens 501b and couples into the single mode fiber 507a (as shown in FIG. 6(a)). In one or more embodiments, the magnification is approximately or about 1, or is 1, in order to couple fiber efficiently because OCT light is delivered with reversible paths (for example, from stator 306b to rotor 306a and from rotor 306a to stator 306b). Coupling efficiency is improved or maximized when having the magnification be approximately or about 1, or be 1.

FIG. 5 shows at least one embodiment of how to couple OCT and excitation channels into a single core of a double clad fiber in a rotary junction. For example, a fiber optic rotary joint may include a single rotator portion having a double clad fiber (e.g., double clad fiber 506) and a lens (e.g., the lens 509 shown in FIG. 5) that operates to collimate OCT light. As aforementioned, a stator portion of a rotary joint may include: (i) an OCT portion having a single mode fiber (e.g., the single mode fiber 507a) and a lens (e.g., the lens 510 shown in FIG. 5) that operates to collimate OCT light, the collimated OCT light coupling into the core of the double clad fiber in the rotator portion; (ii) an excitation stator portion including a single mode fiber (e.g., the single mode fiber 507b) and a lens (e.g., the lens 512 shown in FIG. 5) that operates to have most of the light images in the middle and then the light couples into the core of the double clad fiber 506 in the rotator portion; and (iii) an emission stator portion including a multi-mode fiber 508 and a lens (e.g., the lens 511 as shown in FIG. 5). As shown in FIG. 5, at least one embodiment of the rotary joint or junction may include dichroic filters 502a and 502b along with a mirror 504. The longpass filter 505 as shown in FIG. 4 may be optionally used as needed in one or more embodiments, and one or more embodiments (e.g., as shown in FIG. 5) may not use the longpass filter 505. The longpass filter 505 may be positioned at any predetermined position between the dichroic filter 502b and the GRIN 501d so long as the longpass filter 505 operates to appropriately filter light, for example, by attenuating or stopping shorter wavelengths and by passing or transmitting longer wavelengths as discussed herein. In one or more embodiments, use and positioning of the longpass filter 505 may be application or sample dependent. Preferably, the longpass filter 505 may be used to avoid backward noise and excitation light to achieve a better image when analyzing the fluorescent signal. OCT (e.g., 1.3 um) light is collimated by the lens for the OCT channel (e.g., the lens 510 for the OCT channel) and by the lens for the rotator channel (e.g., the lens 509 for the rotator channel). Focal lengths of both lenses 509, 510 are almost or about the same (or may be the same) to minimize insertion losses. Using a small lens for one or more of the lenses 509 is preferred to miniaturize the rotator channel. Also, using a small lens for one or more of the lenses 510, 511, 512 are preferred to miniaturize the stator channel. In one embodiment, the focal length of the rotator lens 509 may be smaller to achieve better chromatic aberration, and in one or more embodiments, the focal length of the rotator lens 509 may be longer to be less diverging for fluorescence. A secondary image may be used for excitation coupling, and, as discussed further below, one or more fabrication processes may be easier to achieve active alignment of the distance between a lens and a respective fiber. As aforementioned, a second line or cable may be used for fluorescence, and a third line or cable may be used for excitation. In one or more embodiments, a shorter distance may be used for fluorescence to have less vignetting because of diverse fluorescence light from the rotator channel to the stator channel. The numerical aperture (NA) of the fibers 506, 507a, 507b, 508, mode-field diameter of the fibers 506, 507a, 507b, 508 and lens relationship are determined to, preferably maximize (or at least increase or improve) coupling efficiencies for OCT, excitation and fluorescence lights. For OCT, the same or similar focal lengths of lenses 509, 510 are used. For excitation, one or more embodiments may meet the following conditions: $M_{ex}=|f_{rot}/f_{ex}|\leq |MFD_{dcf}/MFD_{ex}|$, $|\gamma_{ex}|\leq NA_{dcf}/NA_{ex}$, where $f_{rot}$ is the focal length of the lens 509, where $f_{ex}$ is the focal length of the lens 512, $MFD_{dcf}$ is the core mode field diameter of the double clad fiber 506, $MFD_{ex}$ is the core mode field diameter of the excitation fiber 507b, $M_{ex}$ is lateral magnification, and $\gamma_{ex}$ is angular magnification. The lateral and angular magnifications meet the following relationship: $M_{ex} \times \gamma_{ex}=1$ so that $|M_{ex}|=|1/\gamma_{ex}|\geq NA_{ex}/NA_{dcf}$. For fluorescence, one or more embodiments may meet the following condition(s): Core diameter of multi-mode fiber 508≥Clad diameter of double clad fiber 506×$M_{em}$, where $M_{em}$ is the lateral magnification between lenses 509 and 511, and meets the following relationship $M_{em}=|f_{em}/f_{rot}|$, where $f_{em}$ is the focal length of the lens 511.

In one or more embodiments, excitation light of 0.633 um wavelength from the single mode fiber 507b is converged with a GRIN lens 501c. The light is focused at the middle, or at a predetermined position (see e.g., focusing position 600 shown in FIG. 6b) of the optical path to the GRIN lens 510b, and then the light is coupled into mostly the core of the double clad fiber 506 with the GRIN lens 510b, as shown in FIG. 4 and FIG. 6b. Also, in one or more embodiments, the lateral magnification ($M_{ex}$) is less than or equal to the mode-field diameter (MFD) ratio of the core of the double clad fiber 506 ($MFD_{dcf}$) and the single mode fiber 507b ($MFD_{ex}$) in order to couple efficiently into the core of double clad fiber 506. In other words, $|M_{ex}|\leq MFD_{dcf}/MFD_{ex}$. Also, in one or more embodiments, the angular magnification is less than (or less than or equal to as discussed below) the NA (numerical aperture) ratio of the single mode fiber 507b ($NA_{ex}$) and the core of the double clad fiber 506 ($NA_{dcf}$) in order to achieve high coupling efficiency. In other words, $|\gamma|\leq NA_{dcf}/NA_{ex}$. In one or more further embodiments, the magnification may be less than or equal to the NA (numerical aperture) ratio of the single mode fiber 507b ($NA_{ex}$) and the core of the double clad fiber 506 ($NA_{dcf}$) in order to achieve high coupling efficiency. In other words, $|\gamma|\leq NA_{dcf}/NA_{ex}$. For example, when a single mode fiber with $MFD_{ex}$ of 3.5 um and $NA_{ex}$ of 0.13 and a double clad fiber with $MFD_{dcf}$ of 9.2 um and $NA_{dcf}$ of 0.14 are used, the lateral magnification with more than or equal to 1.1 and less than or equal to 2.6 are desired to increase coupling efficiency.

Figure 6C:
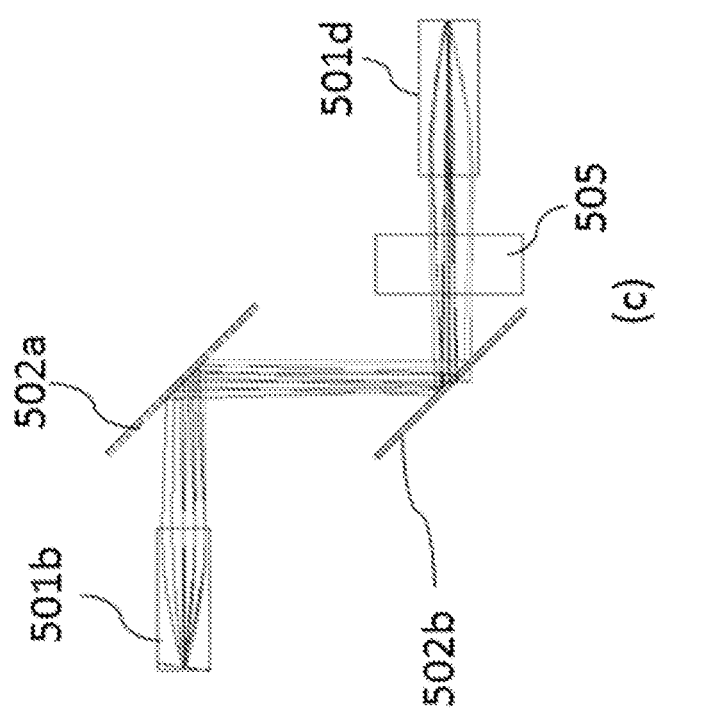

Fluorescence light from mostly the cladding of the double clad fiber 506 is delivered through GRIN lens 510b, as shown in FIG. 6c. The light is diverged due to the cladding diameter and coupled into a multi-mode fiber (e.g., the fiber 508 as shown in FIG. 4) via a GRIN lens 501d (as shown in FIGS. 4 and 6c). In at least one embodiment, high coupling efficiency is achieved with a lateral magnification ($M_{em}$) that is less than or equal to the ratio of the core diameter of the multi-mode fiber 508 ($D_{mm}$) and the cladding diameter 506 ($D_{dcf}$). In other words, $M_{em}\leq D_{mm}/D_{dcf}$.

In at least one embodiment, the OCT light is collimated with GRIN lens 501a and GRIN lens 501b, respectively, in order to achieve less sensitivity when aligning the distances between GRIN lens 501a and GRIN lens 510b. The excitation light, which, in at least one embodiment, is a shorter wavelength than the wavelength of the OCT light, converges and is focused by GRIN lens 501c to an intermediate focus (see e.g., the focusing position 600 of FIG. 6b), and then coupled substantially (e.g., 100%, about 100%, 90%, 80%, about 90% to about 100%, etc.) into the core of the double clad fiber 506. In this configuration, the excitation light couples efficiently into the core of double clad fiber 506, and also the alignment of GRIN lens 501c and single mode fiber 507b becomes easier because GRIN lens 501c and single mode fiber 507b are assembled separately with the assembly of GRIN lens 510b. One or more embodiments of fabrication processes are discussed below.

In some embodiments, the excitation light is a shorter wavelength than the wavelength of the OCT light. For example, the excitation light is at least 20%, 30%, or 40% shorter than the wavelength of the OCT light. Thus, with visible and NIR excitation, the wavelength of the excitation light is, in an exemplary embodiment, at least 400 nm shorter than the wavelength of the OCT light. In one or more alternative embodiments, the excitation light may have a greater wavelength than the wavelength of the OCT light.

In one or more embodiments, as best seen in FIG. 4, dichroic filter 502a is used for separating OCT light from the rest of excitation and fluorescence light. Dichroic filter 502b is used for a separation of the excitation and fluorescence light. The mirror 504 is used to reflect the excitation light. The long-pass filter 505 may be used to filter out back-reflection and/or stray light of excitation light.

Also, the optical path lengths of OCT (Loct), fluorescence (Lfl) and excitation (Lex) light are designed, in at least one embodiment, with the following condition: Loct<Lfl<Lex.

In one or more embodiments, it is preferred to have the OCT optical path length be as short as possible to improve and/or maximize coupling efficiency. It may be difficult to achieve a collimated beam that has a beam waist far (in one or more embodiments, a far beam waist depends on the lens size and quality; for example, in one or more embodiments, >50 mm beam waist may be far whereas, in other embodiments, >50 mm beam waist may not be far) from the collimator lens (see e.g., lens 509 or lens 510 of FIG. 5). In at least one embodiment (best seen in FIG. 6b), excitation light is focused at the middle, or at a predetermined location (e.g., focusing position 600), of the optical path so a longer optical path length may be designed. Fluorescence light is diverged (or diverges) and has a large diameter beam, so, in one or more embodiments, it is preferred to shorten the optical path length of fluorescence light.

In at least one embodiment, wavelengths of excitation light with 350-850 nm and fluorescence light with 400-1200 nm are chosen based on targeted markers. Collagen and/or elastin with an excitation wavelength of 350-400 nm and auto-fluorescence of 400-500 nm are utilized. Lipid and/or fat may be detected with the excitation wavelength of 550-650 nm and fluorescence wavelength of 600-850 nm. ICG (Indocyanine green) marker is used with excitation light with 600-800 nm wavelength and fluorescence light with 750-1200 nm. Any other auto-fluorescence marker(s) and fluorescence dye(s) may be utilized with one or more embodiments of the present disclosure.

Figure 7:
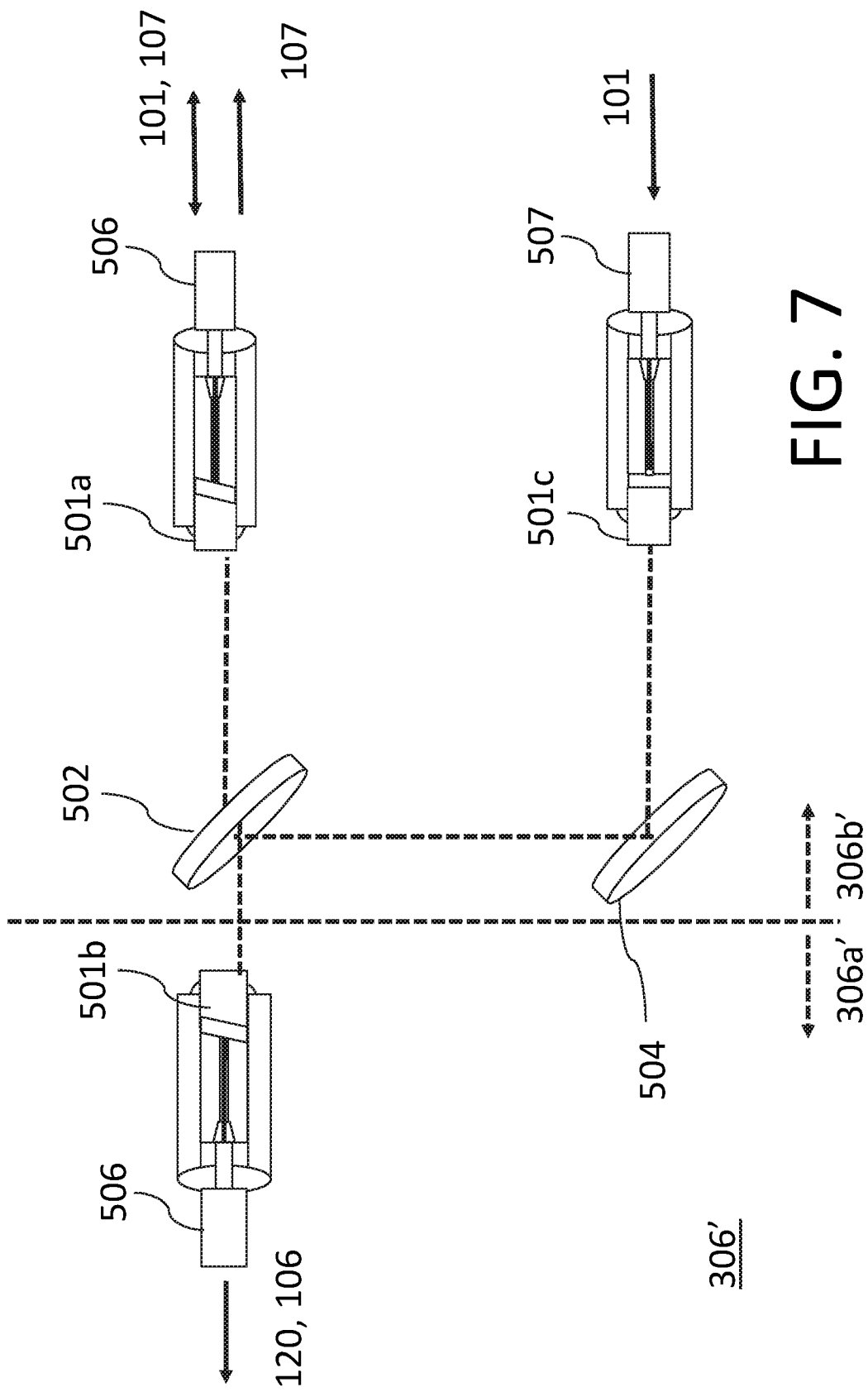
FIG. 7 is a diagram showing at least one embodiment of a free space beam combiner that may be used in at least one embodiment of a fiber optic rotary joint in accordance with one or more aspects of the present disclosure.

In one or more alternative embodiments, a free space beam combiner, which is located inside an FORJ, may be provided as shown in FIG. 7. The embodiment of FIG. 7 is the same as the embodiment shown in FIG. 4, with the following exceptions: the stator 306b' of the rotary junction 306' in FIG. 7 includes two optical fibers (and not three) because the multi-mode fiber 508 and the GRIN lens 501d are removed, and the stator 306b' of the rotary junction 306' includes a double clad fiber 506 being used with GRIN lens 501a (instead of the single mode fiber 507a as shown in FIG. 4). OCT light goes through the core of the double clad fiber 506 in the stator 306', and is then collimated with the GRIN lens 501a. The collimated light is coupled into the core of the double clad fiber 506 in the rotor 306a'. Excitation light, with wavelength shorter than that of OCT light, is converged and focused with the GRIN lens 501c at the middle (or at a predetermined position) of the optical path to GRIN lens 510b. Then, the light is coupled into mostly the core of the double clad fiber 506 in the rotor 306a' of the rotary junction 306'. Fluorescence light from the sample (e.g., the sample 106) is delivered through mostly the clad of the double clad fiber 506 in rotor 306a'. Then, the light is coupled into the clad of the double clad fiber 506 in the stator 306b'. To separate OCT light and fluorescence light, a double clad fiber coupler may be used either inside the PIU 110 or in the imaging subsystem. Dichroic filter 502 of FIG. 7 is used to separate excitation light and the rest of fluorescence and OCT lights. The double clad fiber 506 of the stator 306b' is connected to a core/clad beam splitter to separate OCT and fluorescence light. As such, a simple and compact FORJ may be achieved with this configuration because of a lack of the free-space optical fluorescence channel. Also, it is easier to fabricate the beam combiner because OCT and fluorescence lights are coupled using a common double clad fiber (e.g., the fiber 506). The FORJ 306' may be used in place of the FORJ 306 as discussed above as shown schematically in FIG. 2. In one or more embodiments, a mirror, a ferrule, a sleeve and/or epoxy as discussed in the present disclosure may be optional, and the fibers, lenses and a dichroic filter may be used without one or more of the mirror, the ferrule, the sleeve and/or the epoxy.

Descriptions of like-numbered elements present in the system 100' and/or the rotary junction 306' and already described above, such as for the system 100 and/or the rotary junction 306, shall not be repeated, and are incorporated by reference herein in their entireties.

In at least one embodiment, the console 1200, 1200' operates to control motions of the motor and translation motorized stage (hereinafter referred to as "motor" or "motor and stage") 139, acquires intensity data from the at least one detector(s) 107, and displays the scanned image (e.g., on a monitor or screen such as a display, screen or monitor 1209 as shown in the console 1200 of FIG. 11 and/or the console 1200' of FIG. 12 as further discussed below). In one or more embodiments, the console 1200, 1200' operates to change a speed of the motor 139 and/or to stop the motor 139. The motor 139 may be a stepping or a DC servo motor to control the speed and increase position accuracy.

In one or more embodiments, the console or computer 1200, 1200' operates to control motions of the rotary junction 306, the rotary junction 306', the motor 139, the catheter 120 and/or one or more other above-described components of the system 100 and/or the system 100'. In at least one embodiment, the console or computer 1200, 1200' operates to acquire intensity data from the at least one detector 107 of the OCT sub-system and the fluorescence sub-system, and displays the image(s) (e.g., on a monitor or screen such as a display, screen or monitor 1209 as shown in the console 1200 of FIG. 11 and/or the console 1200' of FIG. 12 as further discussed below). The output of the one or more components of the system 100 and/or the system 100' is acquired with the at least one detector 107 of the OCT sub-system and with the at least one detector 107 of the fluorescence sub-system, e.g., such as, but not limited to, photodiodes, Photomultiplier tube(s) (PMTs), line scan camera(s), or multi-array camera(s). Electrical analog signals obtained from the output of the system 100 and/or the system 100' or one or more components thereof are converted to digital signals to be analyzed with a computer, such as, but not limited to, the computer 1200, 1200' (e.g., as shown in FIGS. 1-2 and 11-12). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light.

Figure 8:
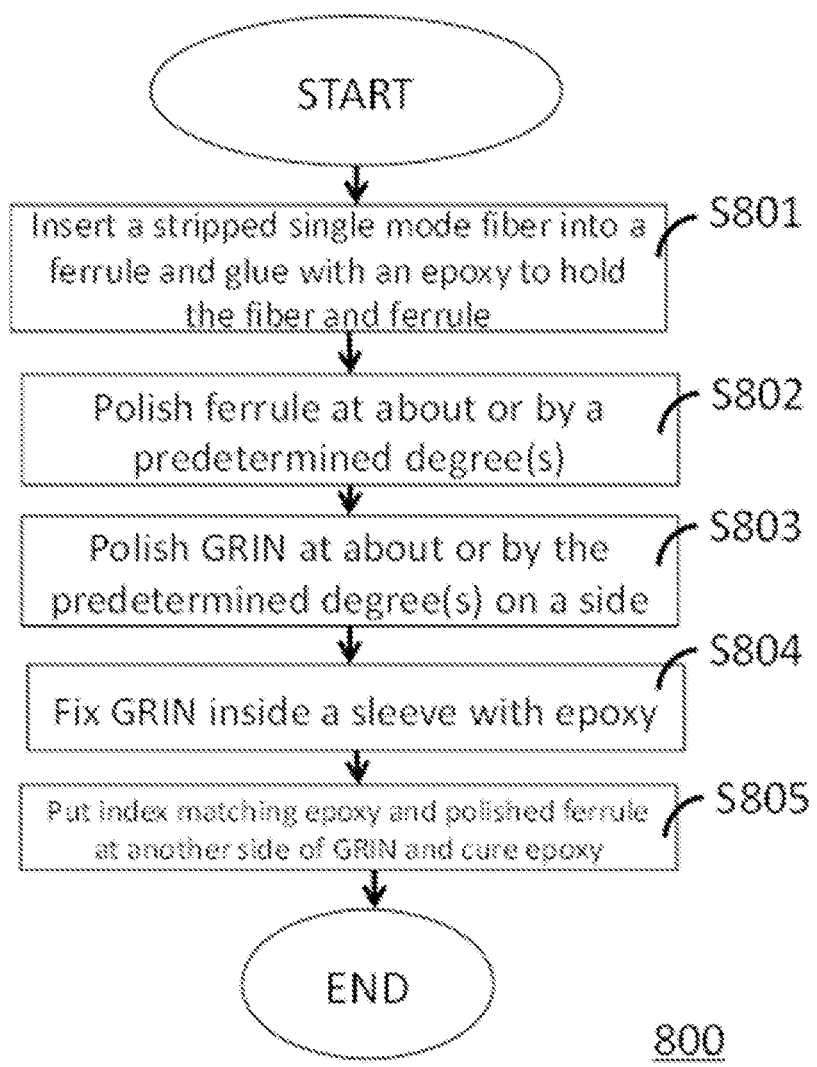
FIG. 8 is a flow chart showing at least one embodiment of a method for making a fiber optic rotary joint in accordance with one or more aspects of the present disclosure.

In accordance with at least one aspect of the present disclosure and as aforementioned, one or more methods for manufacturing or making a fiber optic rotary joint (and/or one or more components thereof) are provided herein. FIG. 8 illustrates a flow chart of at least one embodiment of a method for making one or more components of at least one embodiment of a FORJ. Preferably, the method(s) may include one or more of the following: (i) insert a stripped single mode fiber (see e.g., stripped fiber 900b in portion of FIG. 8a corresponding to step S801 of FIG. 8; see e.g., single mode fiber 507a as aforementioned) into a ferrule (see e.g., ferrule 901 in FIG. 9a) and glue with an epoxy (see e.g., epoxy 902 in FIG. 9a) to hold the fiber and ferrule together (see step S801 of FIG. 8); (ii) polish the ferrule at about or by a predetermined degree(s) (e.g., at or about 8 degrees)

Figure 9A:
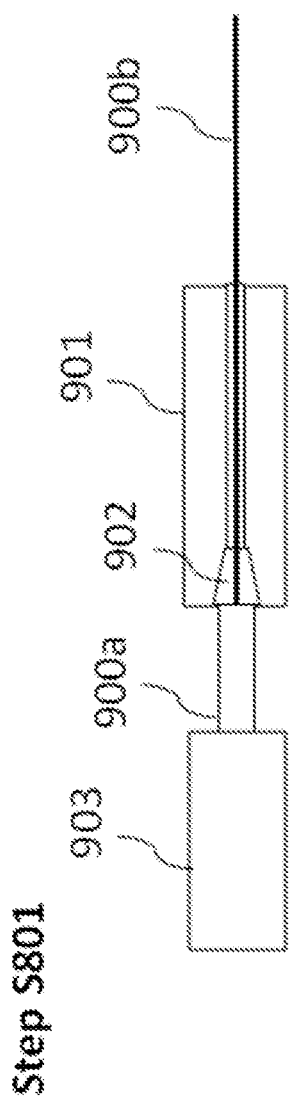
FIGS. 9a-9b are diagrams schematically showing component(s) of steps of a method embodiment of FIG. 8 for making a GRIN collimator that may be used in or with a fiber in a fiber optic rotary joint in accordance with one or more aspects of the present disclosure.
Figure 9A:
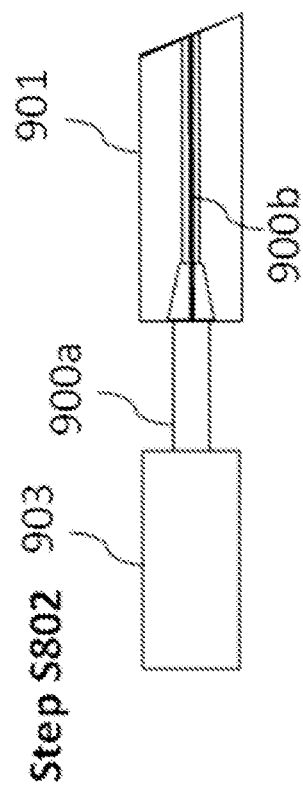
Figure 9A:
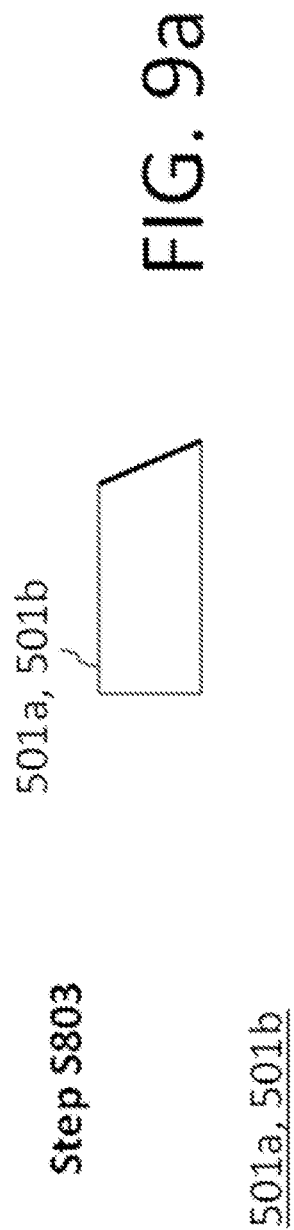
Figure 9B:
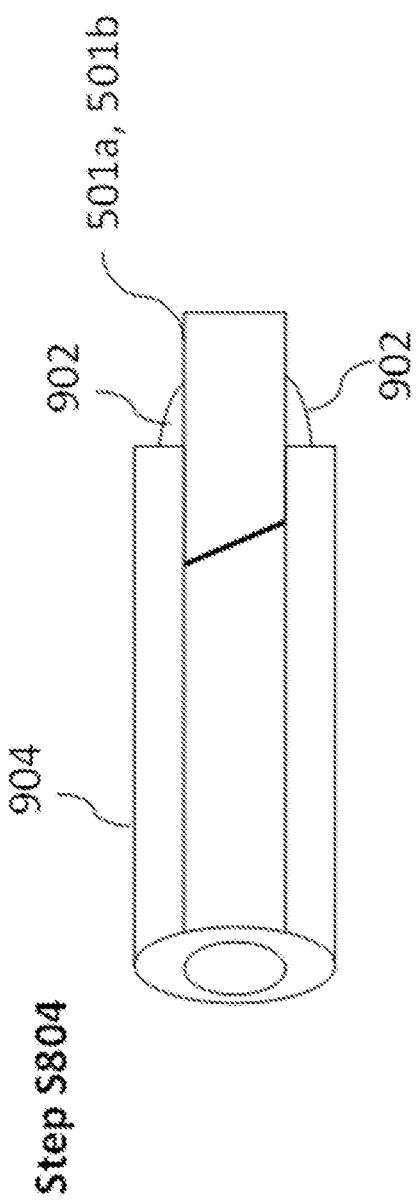
Figure 9B:
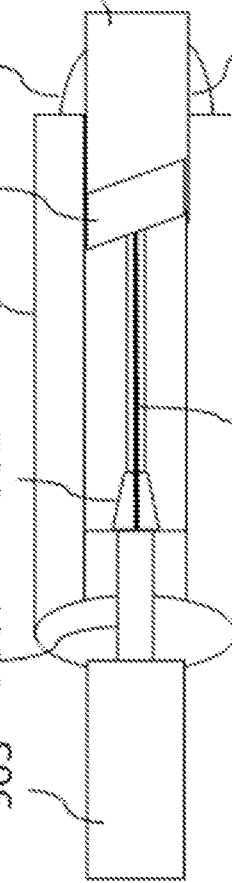
Figure 10:
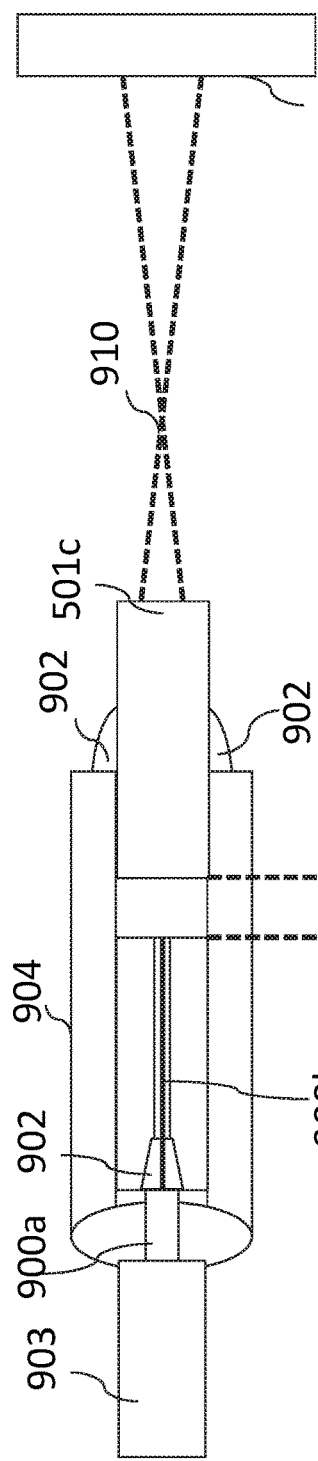
FIG. 10 is a diagram (including portions (a), (b) and (c) thereof) showing an embodiment of fabricating another GRIN collimator of at least one embodiment of a fiber optic rotary joint (and/or one or more components thereof) in accordance with one or more aspects of the present disclosure.
Figure 10:
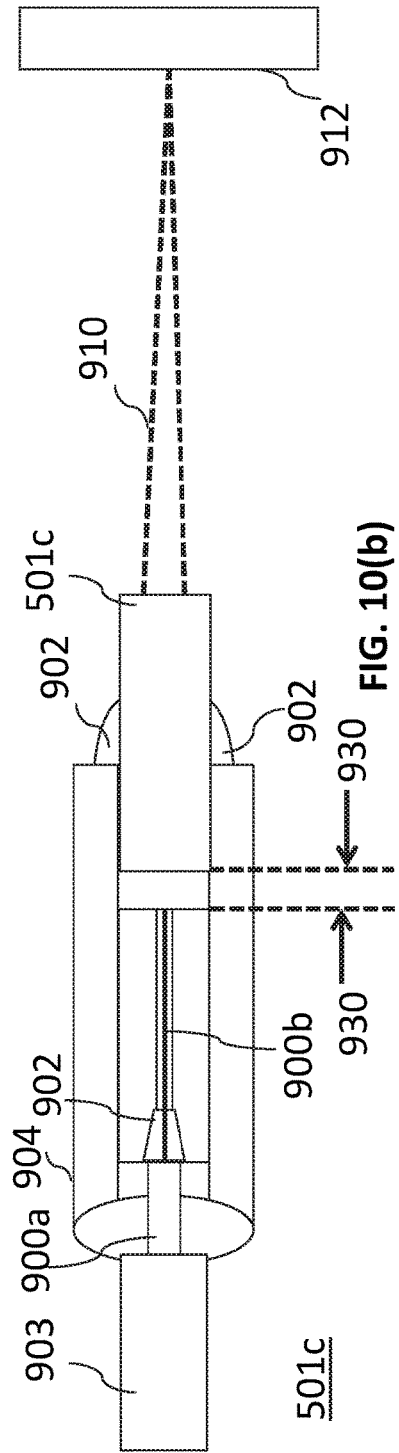
Figure 10:
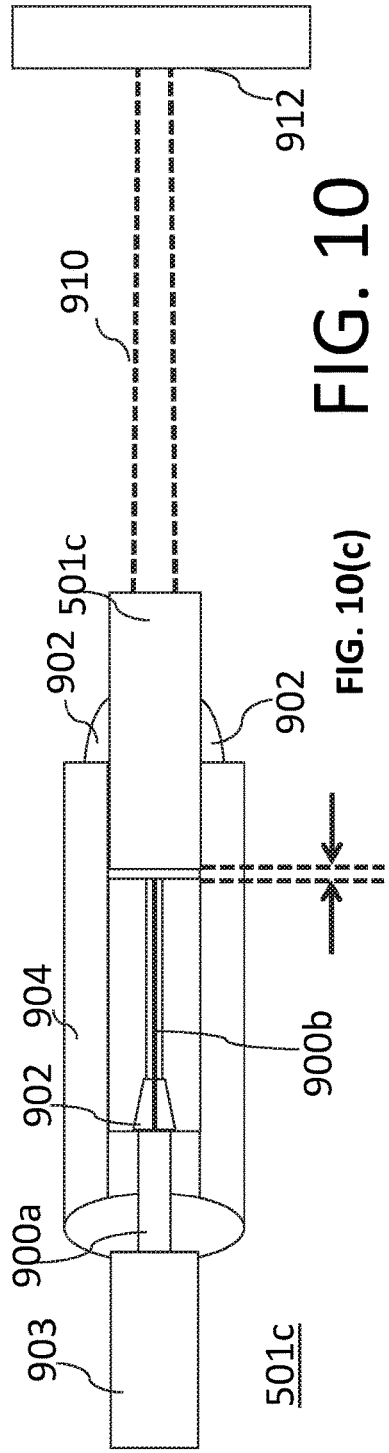

(see step S802 in FIG. 8; see also, e.g., ferrule 901 in portion of FIG. 9a corresponding to step S802); (iii) polish a GRIN (e.g., the GRIN 501a or 501b) at about or by the predetermined degree(s) (e.g., at or about 8 degrees) on a side (see step S803 of FIG. 8; see also, e.g., GRIN 501a, 501b in portion of FIG. 9a corresponding to step S803); (iv) fix the polished GRIN (e.g., the GRIN 501a or 501b) inside a sleeve (e.g., sleeve 904 of FIG. 9b portion corresponding to step S804) with epoxy (e.g., epoxy 902 shown in FIG. 9b portion corresponding to step S804) (see step S804 of FIG. 8); and (v) put gradient index matching (or substantially matching) epoxy (see e.g., the epoxy 902 located in between the polished ferrule 901 and the GRIN (e.g., the GRIN 501a or 501b) inside the sleeve 904 of the portion of FIG. 9b that corresponds to step S805) and polished ferrule (see e.g., the polished ferrule 901) at another side (e.g., on the left side of the sleeve 904) of the polished GRIN (e.g., the GRIN 50a or 501b) and cure the epoxy (e.g., the epoxy 902 at the left side of the sleeve 904) at a predetermined or certain distance of the GRIN (e.g., the GRIN 501a or 501b) and the ferrule (e.g., the ferrule 901) (e.g., in one or more embodiments, the predetermined or certain distance may be about 0.1 mm, about 0 mm-about 1 mm, or any other desired distance depending on the application) to achieve a collimated beam (see step S805 of FIG. 8). The fiber 900a may include a jacket 903 (900 um) as shown in FIGS. 9a-10. In one or more embodiments, the GRIN surface and/or the ferrule surface may be designed at any desirable angle depending on the application for use. In one or more embodiments, the angle of the GRIN 501b and/or GRIN 501a, and/or the ferrule surface, is in the 0-10 degree range.

In one or more embodiments, the surfaces of the single mode fiber (see e.g., the stripped fiber 900b) and the GRIN lens (e.g., the GRIN 501a or 501b) are tilted by the predetermined number of degrees to reduce back-reflection. Gradient index matching (or substantially matching) materials may be placed between the surfaces to reduce the back-reflection. The collimated beam is achieved with the GRIN lens 501a from the single mode fiber (e.g., the single mode fiber 507a as discussed above) to align the distance of the GRIN lens 50a and the fiber 507a.

The method 800 of fabricating a FORJ may further include creating a second GRIN lens (e.g., the GRIN 501b), or creating a second GRIN collimator, by repeating the steps S801-S805 for the second GRIN lens, with the exception being that a different fiber material is used. For example, for GRIN 501b, the aforementioned double clad fiber 506 is used instead of a single mode fiber. The surfaces of the double clad fiber 506 and the GRIN 501b may also be tilted by the predetermined number of degrees (e.g., by or about 8 degrees), and the gradient index matching (or substantially matching) material(s) may be placed between the angled or tilted surfaces of the double clad fiber 506 and the GRIN 510b. In at least one embodiment, a collimated beam is achieved with the GRIN lens 501b from the core of the double clad fiber 506. In one or more embodiments, the GRIN lens 501a and the GRIN lens 501b have approximately the same or the same focal length to achieve magnification of approximately or about 1, or 1, to increase throughput.

The method 800 of fabricating a FORJ may further include creating a third GRIN lens (e.g., the GRIN 501c), or creating a third GRIN collimator fiber. In one or more embodiments, the GRIN collimator (e.g., the GRIN 501c) is fabricated with an active alignment method. A portion of the GRIN 501c may be formed or created using the aforementioned steps regarding a single mode fiber and portions thereof 900a, 900b, 903 and the fixing of same inside a sleeve 904 using epoxy 902 (see such components and the same or similar configuration as shown in FIG. to). As such, the details of such manufacturing steps are incorporated herein by reference in their entireties and are not repeated. The distance between the GRIN 510c and the single mode fiber 507b is aligned to observe a focus position with a camera 912, as best seen in FIG. 10. In at least one embodiment, the camera 912 is placed at the designed certain, or predetermined, distance from GRIN lens 501c, and then a spot size of lights is observed. While changing the distance between GRIN lens 501c and the fiber (see e.g., the stripped portion of the fiber 900b as shown in FIG. to), the distance is fixed when the minimum spot size is observed (see middle portion (b) of FIG. to). In contrast, the distance is adjusted when the spot size is large due to converged beams crossing paths (as shown in top portion (a) of FIG. to) or converging beams not yet being converged (and, therefore, are spaced apart or separated) (as shown in the bottom portion (c) of FIG. to). With the active alignment method, the GRIN 501c collimator is separately fabricated with the GRIN 501b collimator so that these components are easier to fabricate. Also, this fabrication process may achieve a reduction in alignment time.

In one or more embodiments, the method 800 of fabricating a FORJ may further include creating a fourth GRIN lens (e.g., the GRIN 501d), or creating a fourth GRIN collimator fiber. A portion of the GRIN 501d may be formed or created using the aforementioned steps regarding fiber fabrication (using a multi-mode fiber, such as the fiber 508, instead of a single mode fiber) and the fixing of a stripped portion of the multi-mode fiber 508 inside a sleeve 904 using epoxy 902 (see such components and the same or similar configuration as shown in FIG. 10). As such, the details of such manufacturing steps are incorporated herein by reference in their entireties and are not repeated. Moreover, the GRIN 501d collimator is aligned such that the GRIN 501d and the multi-mode fiber 508 may be glued together (e.g., the fiber 508 and the GRIN 501d are touching when glued together). In one or more embodiments, the GRIN 501d and the multi-mode fiber 508 may touch when glued together. In one or more further embodiments, the GRIN 501d and the multi-mode fiber 508 may have air in between when glued together.

Moreover, the method 800 may further include steps to align the GRIN 501a, 501b, 501c, 501d collimators. Preferably, in at least one embodiment, the GRIN 501b collimator is aligned to match (or substantially match) an optical axis and/or mechanical axis of the FORJ 306 or 306' to reduce or minimize rotational variation(s) of insertion loss (es). Then, the rest of the GRIN 501a, 501c, 501d collimators may be mounted to increase or maximize coupling efficiency with tilt and position alignments as discussed herein and as shown in FIGS. 4-8 and 9a-10. Any dichroic filter(s) (e.g., dichroic filter 502, filter 502a, filter 502b, etc.) and/or any mirror(s) (e.g., the mirror 504) may be aligned with the GRIN 501a, 501b, 501c, and/or 501d collimators to achieve increased or maximum coupling efficiency with tilt and position alignments as aforementioned.

A computer, such as the console or computer 1200, 1200', may perform any of the aforementioned steps (e.g., steps S801-S805 for GRIN 501a; repetition of steps S801-S805 for GRIN 501b; the aforementioned steps for GRIN 501c; the aforementioned steps for GRIN 501d and/or alignment of the constructed collimators for GRINs 501a, 510b, 501c and/or 501*d*; etc.), for any system or FORJ being manufactured, including, but not limited to, system 100, system 100', FORJ 306, FORJ 306', etc.

In one or more embodiments, a SEE probe and/or system may use a FORJ (e.g., the FORJ 306, the FORJ 306', etc.) with a connection member or interface module. For example, the connection member or interface module may include a rotary junction for either a SEE probe. In such a SEE system, the rotary junction may be at least one of: a contact rotary junction, a lenseless rotary junction, a lens-based rotary junction, a rotary junction as described herein, etc. The rotary junction may be a one channel rotary junction or a two channel rotary junction. By way of at least one example, in a SEE device one or more light sources may be used, and the light may be split into at least two (2) wavelength ranges for use with one or more embodiments of a FORJ of the present disclosure.

Unless otherwise discussed herein, like numerals indicate like elements. For example, while variations or differences exist between FORJs and/or the systems, such as, but not limited to, the FORJ 306, the FORJ 306', the system 100, the system 100', etc., one or more features thereof may be the same or similar to each other, such as, but not limited to, the light source 101 or other component(s) thereof (e.g., the console 1200, the console 1200', etc.). Those skilled in the art will appreciate that the light source 1ot, the at least one detector 107 and/or one or more other elements of the system 100, may operate in the same or similar fashion to those like-numbered elements of one or more other systems, such as, but not limited to, the system 100', as discussed herein. Those skilled in the art will appreciate that alternative embodiments of the system 100, the system 100', FORJ 306, FORJ 306' and/or one or more like-numbered elements of one of such systems or FORJs, while having other variations as discussed herein, may operate in the same or similar fashion to the like-numbered elements of any of the other systems (or component(s) thereof) or FORJs (or component(s) thereof) discussed herein. Indeed, while certain differences exist between the system 100 and the system 100', and between FORJ 306 and FORJ 306', as discussed herein, there are similarities. Likewise, while the console or computer 1200 may be used in one or more systems (e.g., the system 100, the system 100', a system for manufacturing an FORJ (e.g., the FORJ 306, the FORJ 306', etc.), etc.) and/or to control an FORJ (e.g., the FORJ 306, the FORJ 306', etc.), one or more other consoles or computers, such as the console or computer 1200', may be used additionally or alternatively.

There are many ways to compute rotation, intensity, or any other measurement discussed herein, and/or to control and/or manufacture an FORJ, digital as well as analog. In at least one embodiment, a computer, such as the console or computer 1200, 1200', may be dedicated to control and monitor a FORJ and devices, systems, methods and/or storage mediums for use therewith described herein.

Various components of a computer system 1200 (see e.g., the console or computer 1200 as shown in FIGS. 1-2) are provided in FIG. 11. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 11). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100 and/or the system 100', discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a FORJ, and/or a device, system or storage medium for use with same. The system 1200 may further include one or more processors connected via a network connection (e.g., via network 1206). The CPU 1201 and any additional processor being used by the system 1200 may be located in the same telecom network or in different telecom networks (e.g., performing FORJ manufacturing and/or use technique(s) may be controlled remotely).

The I/O or communication interface 1205 provides communication interfaces to input and output devices, which may include the light source 1ot, a FORJ (e.g., the FORJ 306, the FORJ 306', etc.), a microphone, a communication cable and a network (either wired or wireless), a keyboard 1210, a mouse (see e.g., the mouse 1211 as shown in FIG. 12), a touch screen or screen 1209, a light pen and so on. The Monitor interface or screen 1209 provides communication interfaces thereto.

Any methods and/or data of the present disclosure, such as the methods for using and/or manufacturing a FORJ, and/or a device, system or storage medium for use with same, as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 12), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 11. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 11) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 12. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with a rotary junction (e.g., the FORJ 306, the FORJ 306', etc.), the motor 139 and/or one or more other components of a system (e.g., the system 100, the system 100', etc.) via the operation interface 1214 or the network interface 1212. A computer, such as the computer 1200', may include the FORJ 306 or 306' and/or the motor 139 in one or more embodiments. The operation interface 1214 is connected with an operation unit such as a mouse device 1211, a keyboard 1210 or a touch panel device. The computer 1200' may include two or more of each component.

Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the PUI 110, the rotary junction (e.g., the rotary junction 306, the rotary junction 306', etc.), the motor 139, the catheter 120 and/or one or more other components of a system, such as the system 100, 100', etc., to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a system (e.g., the system 100, the system 100', etc.), for example when performing OCT or other imaging technique. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', etc.) to set or change the imaging condition, and to start or end the imaging. The laser source 101 of an OCT sub-system and/or the laser source 101 of a fluorescence sub-system as aforementioned may have interfaces to communicate with the computers 1200, 1200' to send and receive the status information and the control signals.

The present disclosure and/or one or more components of devices, systems and storage mediums, and/or methods, thereof also may be used in conjunction with any suitable optical assembly including, but not limited to, SEE probe technology, such as in U.S. Pat. Nos. 6,341,036; 7,447,408; 7,551,293; 7,796,270; 7,859,679; 8,45,177; 8,145,018; 8,838,213; 9,254,089; 9,295,391; 9415550; 9,557,154 and Patent Application Publication Nos. US2017/0035281; WO2015/116951; WO2015/116939; WO2017/024145; and US2018/0017778, each of which patents, patent publications and patent application(s) are incorporated by reference herein in their entireties.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2012/0101374 and 2016/0228097, each of which patents, patent publications and patent application(s) are incorporated by reference herein in their entireties.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. A fiber optic rotary joint comprising:
   a beam combiner;
   a rotor that operates to rotate and that includes a common optical fiber connected to or part of the beam combiner; and
   a stator that operates to be stationary in the fiber optic rotary joint and that includes at least two optical fibers, a first of the at least two optical fibers operating to guide at least a first light and being connected to or part of the beam combiner and a second of the at least two optical fibers operating to guide a second light and being connected to or part of the beam combiner, the first light being an imaging modality light or light used to perform Optical Coherence Tomography (OCT) and the second light being an excitation light,
   wherein the beam combiner operates to combine the first and second lights from the at least two optical fibers such that the combined light couples, or substantially couples, and is focused into a core of the common optical fiber.

2. The fiber optic rotary joint of claim 1, wherein one or more of:
   (i) the common optical fiber includes at least two clads or claddings;
   (ii) the common optical fiber is a double clad fiber; and/or
   (iii) the common optical fiber operates to deliver the combined light towards or to a sample, object, or target.

3. The fiber optic rotary joint of claim 1, wherein one or more of:
   (i) the second light has a wavelength that is shorter than a wavelength of the first light;
   (ii) the first light is delivered as a collimated beam at or to the beam combiner; and/or
   (iii) the second light is delivered after focusing in a middle of an optical path from the stator to the rotor.

4. The fiber optic rotary joint of claim 1, wherein:
   (i) the common optical fiber is attached to a lens that operates to couple, or substantially couple, and to focus the combined light into the core of the common optical fiber;
   (ii) the first fiber of the at least two fibers is attached to a lens that operates to collimate the first light; and
   (iii) the second fiber of the at least two fibers is attached to a lens that operates to focus the second light, the focusing occurring at a predetermined position, or in a middle, of an optical path from the second fiber to the common optical fiber.

5. The fiber optic rotary joint of claim 4, wherein one or more of:
   (i) the lens attached to the common optical fiber and the lens attached to the first fiber are approximately the same, or are the same, magnification; and/or
   (ii) at least one lens of the lens attached to the common optical fiber, the lens attached to the first fiber and the lens attached to the second fiber is a gradient-index (GRIN) lens.

6. The fiber optic rotary joint of claim 4, wherein one or more of:
   (i) a lateral magnification ($M_{ex}$) of the lens attached to the second fiber of the stator and the lens attached to the common optical fiber of the rotor is less than or equal to a mode field diameter (MFD) ratio of the core of the common optical fiber ($MFD_{dcf}$) and the second fiber ($MFD_{ex}$) such that $|M_{ex}| \leq MFD_{dcf}/MFD_{ex}$; and/or
   (ii) the lateral magnification ($M_{ex}$) is more than or equal to a numerical aperture (NA) ratio of the second fiber ($NA_{ex}$) and the core of the common optical fiber ($NA_{dcf}$) such that $|M_{ex}| \geq NA_{ex}/NA_{dcf}$.

7. The fiber optic rotary joint of claim 1, wherein:
   (i) the at least two optical fibers of the stator further includes a third optical fiber operating to guide a third light and being connected to or part of the beam combiner;
   (ii) the third light is delivered from the common optical fiber to the third optical fiber of the stator; and
   (iii) propagation lengths of the lights meet the following condition: propagation length of the first light<propagation length of the third light<propagation length of the second light.

8. The fiber optic rotary joint of claim 7, wherein one or more of:
   (i) the common optical fiber is a double clad fiber, the third fiber of the stator is a multi-mode fiber and the third light is delivered from a cladding of the double clad fiber to the multi-mode fiber in the stator; and/or
   (ii) the third light is a fluorescence light from a sample or object.

9. The fiber optic rotary joint of claim 7, further comprising:
   a first lens attached to the common optical fiber, the first lens operating to couple, or substantially couple, and to focus the combined light into the core of the common optical fiber;
   a second lens attached to the first fiber, the second lens operating to collimate the first light;
   a third lens attached to the second fiber, the third lens operating to focus the second light;
   a fourth lens attached to the third fiber;
   a first dichroic filter disposed or positioned in the stator between the first lens and the second lens, the first dichroic filter operating to separate the first light from the second light and the third light; and
   a second dichroic filter disposed or positioned in the stator between the first lens and the second lens, the second dichroic filter operating to separate the second light from the third light.

10. The fiber optic rotary joint of claim 9, further comprising one or more of:
    (i) a longpass filter positioned in between the second dichroic filter and the fourth lens, the longpass filter operating to at least one of: (a) filter light passing through the longpass filter by attenuating or stopping shorter wavelength(s) of light and by passing or transmitting longer wavelength(s) of light; and (b) avoid backward noise by filtering out back-reflection and/or stray light of excitation light to achieve an improved image when analyzing a fluorescent signal; and/or
    (ii) a mirror disposed or positioned in the stator in between the third lens and the second dichroic filter, the mirror operating to reflect the second light.

11. The fiber optic rotary joint of claim 1, wherein one or more of:
    (i) the first fiber is a double clad fiber that operates to guide the first light towards the rotor and to guide light from the rotor away from the rotor and through the stator;
    (ii) the second light has a wavelength that is shorter than a wavelength of the first light;

(iii) the fiber optic rotary joint further comprises a double clad fiber coupler and/or a core or clad beam splitter that operates to separate the first light from a third light, wherein the first light is an imaging light or light used to perform Optical Coherence Tomography (OCT), the second light is an excitation light, and the third light is a fluorescence light from a sample or object;

(iv) the fiber optic rotary joint further comprises:
a first lens attached to the common optical fiber, the first lens operating to couple, or substantially couple, the combined light into the core of the common optical fiber;
a second lens attached to the first fiber, the second lens operating to collimate the first light;
a third lens attached to the second fiber, the third lens operating to focus the second light; and
a dichroic filter disposed or positioned in the stator between the first lens and the second lens, the dichroic filter operating to separate the first light from the second light; and/or (v) the fiber optic rotary joint further comprises a mirror disposed or positioned in the stator in between the third lens and the dichroic filter, the mirror operating to reflect the second light.

12. A Multi-modality fiber optic rotary joint comprising:
a rotor and a static beam combiner,
a first optical fiber and a first lens in the rotor;
a second lens and a second optical fiber in the beam combiner;
a third lens and a third optical fiber in the beam combiner;
wherein:
(i) the first lens and the second lens are configured such that a first wavelength light couples to and from a core of the first optical fiber to a core of the second optical fiber, and
(ii) the first lens and the third lens are configured such that a second wavelength light from a core of the third optical fiber is coupled to the core of the first optical fiber with an intermediate focus in between the first lens and the third lens.

13. The multi-modality fiber optic rotary joint of claim 12, wherein one or more of:
(i) the first optical fiber is a double clad fiber;
(ii) the multi-modality fiber optic rotary joint further comprises a fourth lens and a fourth optical fiber in the beam combiner, wherein the first lens and the fourth lens are configured to couple a third wavelength light from the first optical fiber to the fourth optical fiber; and/or
(iii) one or more of: (a) the third wavelength light propagates in a cladding of the double clad fiber; and/or (b) the third wavelength is between 450 nm to 1.2 um.

14. The multi-modality fiber optic rotary joint of claim 12, wherein at least one lens of the first lens, the second lens and the third lens is one or more of: a gradient-index (GRIN) lens and/or an aspheric lens.

15. The multi-modality fiber optic rotary joint of claim 12, further comprising at least one achromatic filter in the static beam combiner, the at least one achromatic filter operating to separate light with different wavelengths.

16. The multi-modality fiber optic rotary joint of claim 12, wherein one or more of:
(i) the first wavelength light has a wavelength that is longer than the wavelength of the second wavelength light; and/or (ii) at least one of:
(a) the first wavelength light has a wavelength between 1.2 μm and 1.7 μm; and/or
(b) the second wavelength light has a wavelength between 400 nm and 800 nm.

17. An Optical Coherence Tomography (OCT) system using a fiber optic rotary joint (FORJ), the system comprising:
an interference optical system that operates to: (i) receive and divide light from a light source into a first light with which an object or sample is to be irradiated and which travels along a sample arm of the interference optical system and a second reference light, (ii) send the second reference light along a reference arm of the interference optical system for reflection off of a reference reflection of the interference optical system, and (iii) generate interference light by causing reflected or scattered light of the first light with which the object or sample has been irradiated and the reflected second reference light to combine or recombine, and/or to interfere, with each other, the interference light generating one or more interference patterns;
at least one detector that operates to continuously acquire the interference light and/or the one or more interference patterns to measure the interference or the one or more interference patterns between the combined or recombined light; and
a fiber optic rotary joint (FORJ) comprising:
a beam combiner;
a rotor that operates to rotate and that includes a common optical fiber connected to or part of the beam combiner;
a stator that operates to be stationary in the fiber optic rotary joint and that includes at least two optical fibers, a first of the at least two optical fibers operating to guide at least the first light and being connected to or part of the beam combiner and a second of the at least two optical fibers operating to guide a third light and being connected to or part of the beam combiner, the first light being an imaging modality light or light used to perform Optical Coherence Tomography (OCT) and the third light being an excitation light,
wherein the beam combiner operates to combine the first and third lights from the at least two optical fibers such that the combined light couples, or substantially couples, and is focused into a core of the common optical fiber.

18. The system of claim 17, wherein the combined light operates to irradiate the sample, and the FORJ includes at least one dichroic filter to separate the combined light into OCT light to be transmitted to the at least one detector and into fluorescent light to be transmitted to at least another detector.

19. The system of claim 17, further comprising one or more of:
(i) at least two light sources, a first of the at least two light sources operating to produce the first light, which is an OCT light, and a second of the at least two light sources operating to produce the third light, which is an excitation light; and/or
(ii) at least one of a motor and a processor that operates to rotate the rotor of the FORJ.

20. An Optical Coherence Tomography (OCT) system using a fiber optic rotary joint (FORJ), the system comprising:

an interference optical system that operates to: (i) receive and divide light from a light source into a first light with which an object or sample is to be irradiated and which travels along a sample arm of the interference optical system and a second reference light, (ii) send the second reference light along a reference arm of the interference optical system for reflection off of a reference reflection of the interference optical system, and (iii) generate interference light by causing reflected or scattered light of the first light with which the object or sample has been irradiated and the reflected second reference light to combine or recombine, and/or to interfere, with each other, the interference light generating one or more interference patterns;

at least one detector that operates to continuously acquire the interference light and/or the one or more interference patterns to measure the interference or the one or more interference patterns between the combined or recombined light; and a Multi-modality fiber optic rotary joint (FORJ) comprising:
  a rotor and a static beam combiner,
  a first optical fiber and a first lens in the rotor;
  a second lens and a second optical fiber in the beam combiner;
  a third lens and a third optical fiber in the beam combiner;

wherein:
  (i) the first lens and the second lens are configured such that the first light couples to and from a core of the first optical fiber to a core of the second optical fiber, and
  (ii) the first lens and the third lens are configured such that a third light from a core of the third optical fiber is coupled to the core of the first optical fiber with an intermediate focus in between the first lens and the third lens.

21. The system of claim 20, wherein the first light and the third light combine in the beam combiner such that the combined light operates to irradiate the sample, and the FORJ includes at least one dichroic filter to separate the combined light into OCT light to be transmitted to the at least one detector and into fluorescent light to be transmitted to at least another detector.

22. The system of claim 20, further comprising one or more of:
  (i) at least two light sources, a first of the at least two light sources operating to produce the first light, which is an OCT light, and a second of the at least two light sources operating to produce the third light, which is an excitation light; and/or
  (ii) at least one of a motor and a processor that operates to rotate the rotor of the FORJ.

* * * * *